(12) United States Patent
Moreadith et al.

(10) Patent No.: US 8,383,093 B1
(45) Date of Patent: Feb. 26, 2013

(54) SUBCUTANEOUS DELIVERY OF POLY(OXAZOLINE) CONJUGATES

(75) Inventors: Randall Moreadith, Huntsville, AL (US); Michael David Bentley, Huntsville, AL (US); Kunsang Yoon, Madison, AL (US); Zhihao Fang, Madison, AL (US); Rebecca Weimer, Huntsville, AL (US); Bekir Dizman, Huntsville, AL (US); Tacey Viegas, Madison, AL (US)

(73) Assignee: Serina Therapeutics, Inc., Huntsville, AL (US)

(*) Notice: Subject to any disclaimer, the term of this patent is extended or adjusted under 35 U.S.C. 154(b) by 0 days.

(21) Appl. No.: 13/524,994

(22) Filed: Jun. 15, 2012

Related U.S. Application Data

(60) Provisional application No. 61/554,336, filed on Nov. 1, 2011.

(51) Int. Cl.
*A61K 31/00* (2006.01)
(52) U.S. Cl. .................................................. 424/78.3
(58) Field of Classification Search .................. 424/78.3
See application file for complete search history.

(56) References Cited

U.S. PATENT DOCUMENTS

| | | | |
|---|---|---|---|
| 5,880,131 | A | 3/1999 | Greenwald |
| 6,914,121 | B2 | 7/2005 | El-Tayar |
| 7,872,041 | B2 | 1/2011 | Scheller |
| 7,943,141 | B2 | 5/2011 | Harris |
| 8,088,884 | B2 | 1/2012 | Harris |
| 8,101,706 | B2 | 1/2012 | Yoon |
| 8,110,651 | B2 | 2/2012 | Yoon |
| 2011/0121224 | A1 | 5/2011 | Matsushita |
| 2012/0123055 | A1 | 5/2012 | Yoon |
| 2012/0136123 | A1 | 5/2012 | Harris |

FOREIGN PATENT DOCUMENTS

| | | | |
|---|---|---|---|
| EP | 1466627 | | 10/2004 |
| WO | WO99/55376 | | 11/1999 |
| WO | WO2009089542 | * | 7/2009 |

OTHER PUBLICATIONS

Belluzi, J.D., et al. "N-0923, a Selective Dopamine D2 Receptor Agonist, is Effacious in Rat and Monkey Models of Parkinson's Disease" (1994) Movement Disorders vol. 9. No. 2, pp. 147-154.
D'Souza, A.J., et al., "Minireview Release from Polymeric Prodrugs: Linkages and Their Degradation" (Aug. 2004), Journal of Pharmaceutical Sciences, vol. 93, No. 8, pp. 1962-1979.
Stocchi, Fabrizio, et al. "Intermittent vs Continuous Levodopa Administration in Patients with Advanced Parkinson Disease" (2005) Arch Neurol, vol. 62, pp. 905-910.
McLeod, Andrew, et al. "Glucocorticoid-Dextran Conjugates as Potential Prodrugs for Colon-Specific Delivery: Hydrolysis in Rat Gastrointestinal Tract Contents" (1994) Journal of Pharmaceutical Sciences, vol. 83, No. 9, pp. 1284-1288.
Bibbiani, Francesco, et al. "Continuous dopaminergic stimulation reduces risk of motor complications in parkinsonian primates" (2005) Experimental Neurology, vol. 192, pp. 73-78.
Stockwell. K.A., et al. "Continuous delivery of ropinirole reverse motor deficits without dyskinesia induction in MPTP-treated common mamosets" (2008) Experimental Neurology, vol. 211, pp. 172-179.
Stockwell, K.A., et al. "Continuous administration of rotigotine to MPTP-treated common mamosets enhances anti-parkinsonian activity and reduces dyskinesia induction" (2009) Experimental Neurology, vol. 219, pp. 533-542.
Di Stefano, Antonio, et al. "Antiparkinson Prodrugs" (2008) Molecules, vol. 13, pp. 46-68.
Cawello, Will, et al. "Absorption, Disposition, Metabolic Fate, and Elimination of the Dopamine Agonist Rotigotine in Man: Administration by Intravenous Infusion or Transdermal Delivery" (2009) Drug Metabolism and Disposition, vol. 37, No. 10, pp. 2055-2060.
Viegas, Tacey, et al. "Polyoxazoline: Chemistry, Properties, and Applications in Drugy Delivery" (2011) Bioconjugate Chemistry, vol. 22, pp. 976-986.
Li, Xiaoling, et al. "Synthesis of Poly(Hydroxypropylglutamine-Prazosin Carbamate) and Release Studies" (1991) Pharmaceutical Research, vol. 8, No. 4, pp. 527-530.
Duncan, R., et al. "Polymer-drug conjugates: towards a novel approach for the treatment of endrocine-related cancer" (2005) Endocrine-Related Cancer, vol. 12, pp. S189-S199.
Poewe, Werner H., et al. "Efficacy of pramipexole and transdermal rotigotine in advanced Parkinson's disease: a double-blind, double-dummy, randomised controlled trial" (2007) Lancet Neurology, vol. 6, pp. 513-520.
Schmidt, Werner J., et al. "Continuous versus pulsatile administration of rotigotine in 6-OHDA-lesioned rats: contralateral rotations and abnormal involuntary movements" (2008) J Neural Transm, vol. 115, pp. 1385-1392.
Trenkwalder, Claudia, et al. "Efficacy of rotigotine for treatment of moderate-to-severe restless legs syndrome: a randomised, double-blind, placebo-controlled trial" (2008) Lancet Neurology, vol. 7, pp. 595-604.
Joshi, Kasturi "Tansdermal Drug Delivery Systems and Their Use of Polymers" (2008) MatE175—Biomaterials, pp. 1-31.
Li, C., et al. "Polymer-Drug Conjugates: Recent Developments in Clinical Oncology" (2008) Adv. Drug Delivery Reviews, vol. 60, No. 8, pp. 886-898.

* cited by examiner

*Primary Examiner* — David J Blanchard
*Assistant Examiner* — DeVang Thakor
(74) *Attorney, Agent, or Firm* — Thomas G. Peterson; Nicholas J. Landau; Bradley Arant Boult Cummings LLP

(57) ABSTRACT

The present disclosure provides polymer conjugates comprising a polymer and an agent, the agent linked to the polymer via a linking group containing a hydrolyzable moiety.

17 Claims, 3 Drawing Sheets

SUBCUTANEOUS DELIVERY OF POLY(OXAZOLINE) CONJUGATES

FIELD OF THE DISCLOSURE

The present disclosure is related generally to polymer conjugates. The present disclosure relates more specifically to polymer conjugates comprising a poly(oxazoline) polymer and an agent, the agent linked to the poly(oxazoline) polymer by a releasable, hydrolyzable linker. Methods of using such conjugates for the treatment and methods for the preparation of such conjugates are also provided.

BACKGROUND AND PRIOR ART

Development of drug conjugates with water-soluble polymers can enhance the properties of the drugs, including water-solubility, pharmacokinetics, metabolism, bio-distribution, and bioactivity. A number of polymer-protein conjugates having stable linkages have been approved by FDA and are currently valuable medicines (Bentley, M. D. et al., Poly(ethylene) Glycol Conjugates of Biopharmaceuticals in Drug Delivery, in Knablein, J. (ed.), Modern Biopharmaceuticals, Wiley-VCH Verlag GbH, Volume 4, 2005, Chapter 2, pp. 1393-1418). Conjugation of water-soluble polymers including poly(ethylene glycol), poly(glutamate), and poly(hydroxypropylmethacrylate) with small molecule oncolytics has led to several products in clinical trials, but as yet, no marketed drugs (Mero, A., PEG: a useful technology in anticancer therapy, in Veronese, F. M. (ed.), PEGylated Protein Drugs: Basic Science and Clinical Application, Birkhauser Verlag, Basel, 2009, pp. 273-281). Unlike the case of protein conjugates, it is frequently useful to formulate small-molecule conjugates with releasable, hydrolyzable linkages. These polymer conjugates are known to significantly extend the half-lives of the attached small molecules. When the oncolytic drug, irinotecan, was attached to a multi-arm polyethylene glycol polymer, and injected intravenously to mice the plasma half-life of its active metabolite SN-38 was increased from 2 hours to 17 days (Eldon, M. A. et al., Anti-tumor activity and pharmacokinetics of NKTR-102, PEGylated-irinotecan conjugate, in irinotecan-resistant tumors implanted in mice, Poster number: P-0722, presented at the 14th European Cancer Conference (ECCO 14), 23-27 Sep. 2007, Barcelona, Spain).

The advantage of polymer conjugates of small molecule drugs derives from the typically short in vivo half-life of the drug. The short half-lives of these drugs require frequent dosing of several times daily which results in "pulses" of high concentration of the drug, followed by longer periods where the drug concentration in the blood stream is below the amount required for therapeutic efficacy. For example, in some cases, such as Parkinson's disease (PD), pulsatile stimulation of striatal dopamine receptors with short-acting dopamine agonists or levodopa may actually accelerate molecular and physiological changes that lead to degeneration of dopaminergic neurons in the central nervous system (CNS), thus promoting motor fluctuations (dyskinesias) that can be disabling. Physiological levels that are maintained at a steady state without phasic peak and trough levels have been shown to eliminate these side effects in both animals and humans. Low solubility of some of these compounds, combined with limited oral bioavailabity, further complicates their clinical use. These problems are largely solved by preparation of a soluble polymer conjugate.

The art is lacking a polymer conjugate composition suitable for subcutaneous injection that is able to provide sustained, controllable delivery of an agent over a period of days to weeks. The present disclosure provides polymer conjugates comprising a poly(oxazoline) polymer and an agent, the agent linked to the polymer via a linker containing a hydrolyzable moiety. As shown herein, subcutaneous injection of such a polymer conjugate provides sustained delivery of the agent at therapeutically effective levels of a drug over a time period of days to weeks.

SUMMARY OF THE DISCLOSURE

Figure 1A:
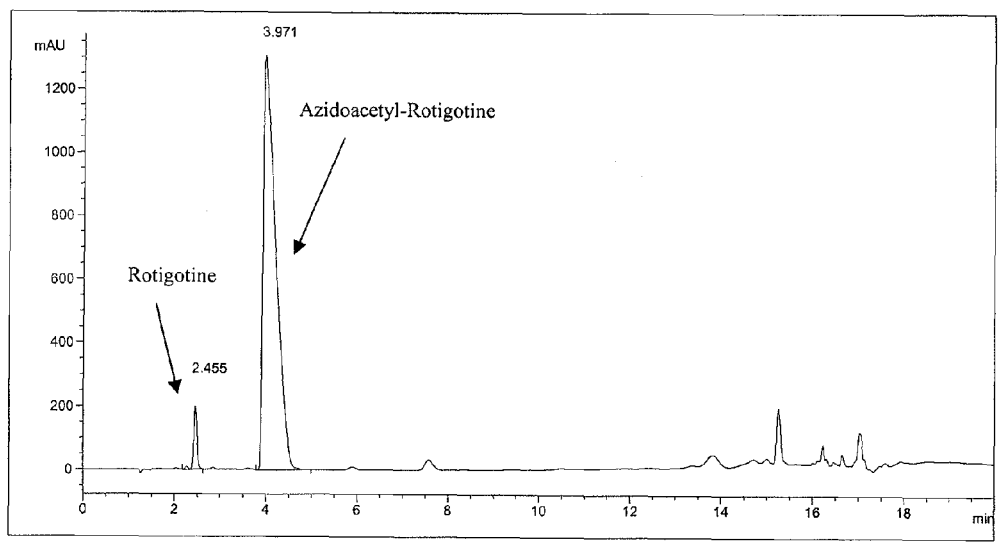
FIG. 1A shows an HPLC chromatogram of azidoacetyl-rotigotine before reversed phase chromatography purification

In a first aspect, the present disclosure provides a polymer conjugate comprising a poly(oxazoline) polymer and an agent, whereby the agent is linked to the polymer by a releasable, hydrolyzable linker so that the agent is releasable from the poly(oxazoline) polymer in vivo upon administration of the polymer conjugate to a subject.

In a second aspect, the present disclosure provides a polymer conjugate comprising a poly(oxazoline) polymer and an agent useful in the treatment of Parkinson's Disease (PD) or other diseases or conditions related to dopamine insufficiency in the peripheral or central nervous system, whereby the agent is linked to the polymer by a releasable, hydrolyzable linker so that the agent is releasable from the poly(oxazoline) polymer in vivo upon administration of the polymer conjugate to a subject.

In a third aspect, the present disclosure provides a polymer conjugate comprising a poly(oxazoline) polymer and a dopamine agonist, whereby the dopamine agonist is linked to the poly(oxazoline) polymer by a releasable, hydrolyzable linker so that the dopamine agonist is releasable from the poly(oxazoline) polymer in vivo upon administration of the polymer conjugate to a subject.

In a fourth aspect, the present disclosure provides a polymer conjugate comprising a poly(oxazoline) polymer and rotigotine, whereby the rotigotine is linked to the poly(oxazoline) polymer by a releasable, hydrolyzable linker so that the rotigotine is releasable from the poly(oxazoline) polymer in vivo upon administration of the polymer conjugate to a subject.

In a fifth aspect, the present disclosure provides a polymer conjugate comprising a poly(oxazoline) polymer and ropinirole, whereby the ropinirole is linked to the poly(oxazoline) polymer by a releasable, hydrolyzable linker so that the ropinirole is releasable from the poly(oxazoline) polymer in vivo after administration of the polymer conjugate to a subject.

In any of the first through fifth aspects, the releasable, hydrolyzable linker provides for release of the agent in vivo after administration of the polymer conjugate to a subject. The releasable, hydrolyzable linker contains a hydrolyzable moiety. In one embodiment of these aspects, the releasable, hydrolyzable linker may be a direct linkage between a functional group on the agent and a functional group on the polymer. In such an embodiment, the hydrolyzable moiety is formed as a result of the linkage between the functional group on the agent and a functional group on the polymer. In another embodiment of these aspects, the releasable, hydrolyzable linker is linking group that contains a hydrolyzable moiety as well as other chemical groups. In such an embodiment, a first functional group on the releasable, hydrolyzable linker forms a linkage with the polymer and a second functional group on the releasable, hydrolyzable linker forms a linkage with the agent. The hydrolyzable moiety may be formed as a result of such linkages or may be present in the releasable, hydrolyzable linker. In one embodiment of these aspects, the hydrolyzable moiety is cleaved in vivo after administration of the polymer conjugate to a subject. In one embodiment of these aspects, the hydrolyzable moiety is a carboxylate ester, a carbonate ester, a carbamate, a disulfide, a sulfide, an acetal, a hemiacetal, a phosphate, a phosphonate or an amide. In a particular embodiment, hydrolyzable moiety is an ester.

In the second aspect, exemplary agents useful in the treatment of PD or other diseases or conditions related to dopamine insufficiency in the peripheral or central nervous include dopamine agonists. Exemplary dopamine agonists include, but are not limited to, rotigotine, pramipexole, quinagolide, fenoldopam, apomorphine, 5-OH-DPAT, ropinirole, pergolide, cabergoline, and bromocriptine.

In the third aspect, exemplary dopamine agonists include, but are not limited to, rotigotine, pramipexole, quinagolide, fenoldopam, apomorphine, ropinirole, pergolide, cabergoline, and bromocriptine.

In the fourth aspect, the rotigotine is (−)rotigotine.

In the first aspect, the agent may be a diagnostic agent or a therapeutic agent. In one embodiment of this aspect, the therapeutic agent is an organic small molecule.

In a sixth aspect, the present disclosure provides a method of treatment for a disease, the method comprising the step of administering a conjugate of the first through fifth aspects to a subject.

In a seventh aspect, the present disclosure provides a method of treatment for a disease, the method comprising the step of administering a conjugate of the first through fifth aspects to a subject, wherein the level of the agent in the bloodstream is controlled by the nature of the linking group, the dose of the polymer conjugate administered, the size of the polymer, the method of administration or a combination of the foregoing.

In an eighth aspect, the present disclosure provides a method of treatment for PD or other diseases or conditions related to dopamine insufficiency in the peripheral or central nervous system, the method comprising the step of administering a conjugate of the first through fifth aspects to a subject.

In a ninth aspect, the present disclosure provides a method of treatment for PD or other diseases or conditions related to dopamine insufficiency in the peripheral or central nervous system, the method comprising the step of administering a conjugate of the first through fifth aspects to a subject, wherein the level of the agent in the bloodstream is controlled by the nature of the linking group, the dose of the polymer conjugate administered, the size of the polymer, the method of administration or a combination of the foregoing.

In a tenth aspect, the present disclosure provides a method of treatment for PD, the method comprising the step of administering a conjugate of the first through fifth aspects to a subject.

In an eleventh aspect, the present disclosure provides a method of treatment for PD, the method comprising the step of administering a conjugate of the first through fifth aspects to a subject, wherein the level of the agent in the bloodstream is controlled by the nature of the linking group, the dose of the polymer conjugate administered, the size of the polymer, the method of administration or a combination of the foregoing.

In any of the sixth through eleventh aspects, the polymer conjugate is administered to a subject by subcutaneous administration.

In any of the sixth through eleventh aspects, the levels of the released agent in the plasma of a subject are controlled by the dose of polymer conjugate delivered via the subcutaneous route.

In any of the eleventh through sixteenth aspects, the method of treatment provides sustained, controllable delivery of the agent over a period of days to weeks.

In any of the eleventh through sixteenth aspects, the method of treatment may further comprise identifying a subject in need of such treatment.

In any of the eleventh through sixteenth aspects, the conjugate is administered in a therapeutically effective amount.

In a twelfth aspect, the present disclosure provides for methods of manufacture of a conjugate of the first through tenth aspects.

In a thirteenth aspect, the present disclosure provides for kits containing a conjugate of the first through fifth aspects along with instructions for administering the conjugate.

DETAILED DESCRIPTION

Definitions

As used herein, the term "agent" refers to any molecule having a therapeutic or diagnostic application, wherein the agent is capable of forming a linkage with a functional group on a poly(oxazoline) polymer or a linking group. In one embodiment, the agent is a diagnostic agent. In one embodiment, the agent is a therapeutic agent. In one embodiment, the therapeutic agent is an organic small molecule. In a specific embodiment, the therapeutic agent is a dopamine agonists. In a further specific embodiment the therapeutic agent is rotigotine. In a further specific embodiment the therapeutic agent is (−)rotigotine. In a further specific embodiment the therapeutic agent is ropinirole.

As used herein, the term "link", "linked" "linkage" or "linker" when used with respect to a polymer or agent described herein, or components thereof, refers to groups or bonds that normally are formed as the result of a chemical reaction and typically are covalent linkages.

As used herein, the term "hydrolyzable" as is used in the phrases "hydrolyzable moiety" and "releasable, hydrolyzable linker" refers to a chemical linkage that is cleavable in a subject under physiological conditions in the subject after a conjugate of the present disclosure has been administered to the subject. In one embodiment, hydrolyzable refers to chemical cleavage. In one embodiment, hydrolyzable refers to cleavage by a substance that is naturally present or induced to be present in the subject. In an aspect of this embodiment, such a substance is an enzyme or polypeptide. Therefore, in one embodiment, hydrolyzable refers to an enzymatic cleavage. In one embodiment, hydrolyzable refers to a combination of the foregoing.

As used herein, the term "alkyl", whether used alone or as part of a substituent group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl" refers to alkyl groups that do not contain heteroatoms.

As used herein, the term "substituted alkyl" refers to alkyl groups as defined above in which one or more bonds to a carbon(s) or hydrogen(s) are replaced by a bond to non-hydrogen or non-carbon atoms such as, but not limited to, an oxygen atom in groups such as hydroxy groups, alkoxy groups and aryloxy groups; a sulfur atom in groups such as, alkyl and aryl sulfide groups, sulfone groups, sulfonyl groups, and sulfoxide groups; a silicon atom in groups such as in trialkylsilyl groups, dialkylarylsilyl groups, alkyldiarylsilyl groups, and triarylsilyl groups; and other heteroatoms in various other groups.

As used herein, the term "unsubstituted aralkyl" refers to unsubstituted alkyl or alkenyl groups as defined above in which a hydrogen or carbon bond of the unsubstituted or substituted alkyl or alkenyl group is replaced with a bond to a substituted or unsubstituted aryl group as defined above. For example, methyl (CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "unsubstituted heterocyclylalkyl" refers to unsubstituted alkyl or alkenyl groups as defined above in which a hydrogen or carbon bond of the unsubstituted alkyl or alkenyl group is replaced with a bond to a substituted or unsubstituted heterocyclyl group. For example, methyl (CH$_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

As used herein, the term "substituted heterocyclylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below.

As used herein, the term "substituted heterocyclyl" has the same meaning with respect to unsubstituted heterocyclyl groups that substituted alkyl groups had with respect to unsubstituted alkyl groups. However, a substituted heterocyclyl group also includes heterocyclyl groups in which one of the carbons is bonded to one of the non-carbon or non-hydrogen atom, such as, but not limited to, those atoms described above with respect to a substituted alky and substituted aryl groups and also includes heterocyclyl groups in which one or more carbons of the heterocyclyl group is bonded to a substituted and/or unsubstituted alkyl, alkenyl or aryl group as defined herein. This includes bonding arrangements in which two carbon atoms of an heterocyclyl group are bonded to two atoms of an alkyl, alkenyl, or alkynyl group to define a fused ring system. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the terms "prevention", "prevent", "preventing", "suppression", "suppress" and "suppressing" refer to a course of action (such as administering a conjugate or pharmaceutical composition) initiated prior to the onset of a symptom, aspect, or characteristics of a disease or condition so as to prevent or reduce such symptom, aspect, or characteristics. Such preventing and suppressing need not be absolute to be useful.

As used herein, the terms "treatment", "treat" and "treating" refers a course of action (such as administering a conjugate or pharmaceutical composition) initiated after the onset of a symptom, aspect, or characteristics of a disease or condition so as to eliminate or reduce such symptom, aspect, or characteristics. Such treating need not be absolute to be useful.

As used herein, the term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, the term "in need of prevention" refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

As used herein, the term "individual", "subject" or "patient" refers to any animal, including mammals, such as mice, rats, other rodents, rabbits, dogs, cats, swine, cattle, sheep, horses, or primates, and humans. The term may specify male or female or both, or exclude male or female.

As used herein, the term "therapeutically effective amount" refers to an amount of a conjugate, either alone or as a part of a pharmaceutical composition, that is capable of having any detectable, positive effect on any symptom, aspect, or characteristics of a disease or condition. Such effect need not be absolute to be beneficial.

General Description

The present disclosure provides polymer conjugates consisting of, consisting essentially of or comprising a poly(oxazoline) polymer and an agent whereby the agent is linked to the polymer by a releasable, hydrolyzable linker so that the agent is releasable from the poly(oxazoline) polymer in vivo upon administration of the polymer conjugate to a subject.

Description of Polymer Conjugates

In a particular embodiment, the polymer conjugates of the present disclosure may be represented by the general formula I.

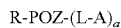

R-POZ-(L-A)$_a$     I wherein,
R is an initiating group;
POZ is a poly(oxazoline) polymer of the formula —[N(COR$_2$)CH$_2$CH$_2$]$_n$— containing at least one reactive group capable of forming a linkage with an agent or a linking group (for example, the releasable, hydrolyzable linker);
R$_2$ is independently selected for each repeating unit from an unsubstituted or substituted alkyl, alkenyl, alkynyl, alaralkyl or heterocyclylalkyl group and n is from 1-1000;
L is a releasable, hydrolyzable linker containing a hydrolyzable moiety;
a is 1 to 50; and
A is an agent.

In certain embodiments, the agent is a diagnostic agent or a therapeutic agent. In certain embodiment, the therapeutic agent is an organic small molecule. In one embodiment, the agent is a compound useful in the treatment of PD or other diseases or conditions related to dopamine insufficiency in the peripheral or central nervous system. Exemplary agents useful in the present disclosure are described herein. In one embodiment, the agent is a dopamine agonists. In one embodiment, the agent is rotigotine. In one embodiment, the agent is (−)rotigotine. In one embodiment, the agent is ropinirole.

As discussed herein, the releasable, hydrolyzable linker provides for release of the agent in vivo after administration of the polymer conjugate to a subject. The releasable, hydrolyzable linker contains a hydrolyzable moiety. In one embodiment, the releasable, hydrolyzable linker may be a direct linkage between a functional group on the agent and a functional group on the polymer. In such an embodiment, the hydrolyzable moiety is formed as a result of the linkage between the functional group on the agent and a functional group on the polymer. In another embodiment, the releasable, hydrolyzable linker is a linking group that contains a hydrolyzable moiety as well as other chemical groups. In such an embodiment, a first functional group on the releasable, hydrolyzable linker forms a linkage with the polymer and a second functional group on the releasable, hydrolyzable linker forms a linkage with the agent. The hydrolyzable moiety may be formed as a result of such linkages or may be present in the releasable, hydrolyzable linker.

In one embodiment, the hydrolyzable moiety is a carboxylate ester, a carbonate ester, a carbamate, a disulfide, a sulfide, an acetal, a hemiacetal, a phosphate, a phosphonate or an amide. In a particular embodiment, the hydrolyzable moiety is an ester.

Regardless of the form of the linkage linking the agent to the polymer, the linkage is a releasable, hydrolyzable linkage that allows the agent to be released from the polymer in vivo at some point after administration of the conjugate to a subject via cleavage of the hydrolyzable moiety. Such releasable, hydrolyzable linkage and hydrolyzable moieties are discussed herein. The release kinetics of the agent from the conjugate provides sustained, controllable delivery of the agent over a period of days to weeks. In one embodiment, the release kinetics of the agent from the polymer is controlled by the nature of the linking group, the dose of the polymer conjugate administered, the size of the polymer, the method of administration or a combination of the foregoing.

The releasable, hydrolyzable linker may form linkages with any reactive group on the polymer backbone. The linkage between the releasable, hydrolyzable linker and the polymer may be formed on a terminal end of the polymer. Alternatively, the linkage between the releasable, hydrolyzable linker and the polymer may be formed using a side chain group of the polymer (referred to herein as a "pendent" position).

Exemplary R groups include, but are not limited to, hydrogen, alkyl and substituted alkyl groups. In one embodiment, the R group is an alkyl group, such as a C1 to C4 alkyl group. In a specific embodiment of the foregoing, the R group is a methyl group. In another embodiment, the R group is H. In yet another embodiment, the R group is selected to lack a functional group. Additional exemplary R groups are disclosed in U.S. Pat. Nos. 8,110,651, 8,101,706, 8,088,884 and 7,943,141 and U.S. patent application Ser. No. 13/003,306, each of which is hereby incorporated by reference for such teaching.

In a particular embodiment, the POZ conjugate of the present disclosure may be represented by the general formula II, wherein the linkage between the linking group and the polymer is formed at the "pendent" position.

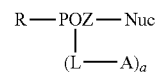

wherein
R is an initiating group;
POZ is a poly(oxazoline) polymer of the formula —[N(COR$_2$)CH$_2$CH$_2$]$_n$— containing at least one reactive group capable of forming a linkage with an agent or a linking group (for example, the releasable, hydrolyzable linker);
R$_2$ is independently selected for each repeating unit from an unsubstituted or substituted alkyl, alkenyl, alkynyl, alaralkyl or heterocyclylalkyl group and n is from 1-1000;
L is a releasable, hydrolyzable linker containing a hydrolyzable moiety;
a is 1 to 50;
A is an agent; and
Nuc is a terminating nucleophile.

Exemplary R groups include, but are not limited to, hydrogen, alkyl and substituted alkyl groups. In one embodiment, the R group is an alkyl group, such as a C1 to C4 alkyl group. In a specific embodiment of the foregoing, the R group is a methyl group. In another embodiment, the R group is H. In yet another embodiment, the R group is selected to lack a functional group. Additional exemplary R groups are disclosed in U.S. Pat. Nos. 8,110,651, 8,101,706, 8,088,884 and 7,943,141 and U.S. patent application Ser. No. 13/003,306, each of which is hereby incorporated by reference for such teaching.

The Nuc group may contain a second functional group or be inert. When Nuc contains a functional group, exemplary groups include, but are not limited to, alkyne, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). When Nuc contains an inert group, any inert group may be used, including, but not limited to —$C_6H_5$.

In one embodiment, Nuc is —S—$CH_2$—$C_6H_5$ and Nuc is inert.

In one embodiment, Nuc has the structure Z-B-Q and the POZ conjugate of the present disclosure may be represented by the general formula IIa

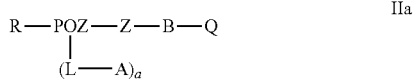

wherein
Z is S, O, or N;
B is an optional linking group; and
Q is a terminal portion of a terminating nucleophile; in certain embodiments Q is inert (i.e., does not contain a functional group); in other embodiments, Q contains a second functional group.

Exemplary B groups include, but are not limited to, alkylene groups. In a particular embodiment, B is —$(CH_2)_y$— where y is an integer selected from 1 to 16.

In a particular embodiment, Z is S. POZ conjugates containing a sulfur group as described herein may be prepared by terminating the POZ cation with a mercaptide reagent, such as, but not limited to, a mercapto-ester (for example, —S—$CH_2CH_2$—$CO_2CH_3$) or mercapto-protected amine (for example, —S—$CH_2CH_2$—NH-tBoc). Such POZ conjugates provide for effective, large-scale purification by ion-exchange chromatography (to remove secondary amines), as well as allowing for control of polydispersity values (with polydispersity values of 1.10 or less) and for the creating of conjugates with higher molecular weight POZ polymers. In another embodiment, Z is N. In a further embodiment, Z is O.

As stated above, Q may be inert or may contain a functional group. When Q contains a functional group, exemplary groups include, but are not limited to, alkyne, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). When Q is an inert group, any inert group may be used, including, but not limited to —$C_6H_5$.

In one embodiment, L contains a hydrolyzable moiety and Z is S. In another specific embodiment L contains a hydrolyzable moiety, and Z is O. In still another specific embodiment L contains a hydrolyzable moiety, and Z is N.

A variety of POZ polymers may be used in the POZ conjugates of the present disclosure. The POZ may contain a single type or class of functional groups or may contain more than one type or class of functional groups. The POZ be a linear POZ polymer, a branched POZ polymer, a pendent POZ polymer or a multi-armed POZ polymer. Various representative POZ polymers are described herein. The POZ polymer may be prepared by living cation polymerization as described in U.S. Pat. Nos. 8,110,651, 8,101,706, 8,088,884 and 7,943,141 and U.S. patent application Ser. No. 13/003,306, each of which is hereby incorporated by reference for such teaching. In one embodiment, the POZ polymer is prepared by living cation polymerization.

In one embodiment of the foregoing, the POZ polymer has the formula $R_1$—{[N(COX)$CH_2CH_2$]$_o$—[N(COR$_2$)$CH_2CH_2$]$_m$}$_a$—,
wherein
X is a pendent moiety containing a functional group capable of forming a linkage with the releasable hydrolyzable linker or the agent (thereby forming the releasable hydrolyzable linker);
$R_2$ is a group that is not reactive with the agent or the releasable hydrolyzable linker;
a is ran which indicates a random copolymer or block which indicates a block copolymer
o is an integer from 1 to 50; and
m is an integer from 1 to 950.

In this embodiment, the agent or releasable hydrolyzable linker forms a linkage with X, the pendent moiety containing a functional group capable of forming a linkage with the linking group. Exemplary functional groups for X include, but are not limited to, alkyne, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). X may comprise a linking portion that links the functional group to the poly (oxazoline) polymer. Exemplary linking portions include alkylene groups. In certain cases, the alkylene group is a $C_1$-$C_{15}$ alkylene group.

In a particular embodiment, X contains an alkyne group and the releasable hydrolyzable linker contains an azido group. In another embodiment, X contains an azido group and the releasable hydrolyzable linker contains an alkyne group. In still a further embodiment, X contains a carboxylic acid group and the releasable hydrolyzable linker contains a phenolic group.

In a particular embodiment, $R_2$ is H, alkyl or substituted alkyl.

In a particular embodiment, the POZ conjugate of the general formula II can be represented as a compound of the formula IIa:

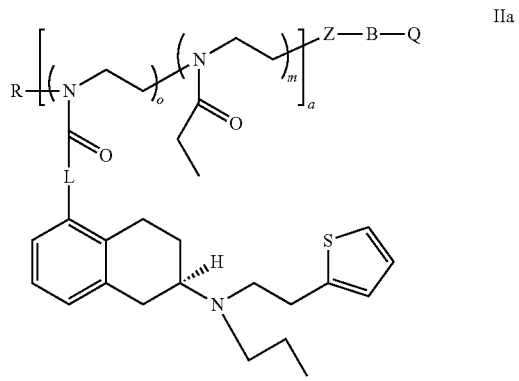

wherein in the variable groups are as defined above.

In a particular embodiment, the POZ conjugate of the general formula II can be represented as a compound of the formula IIb:

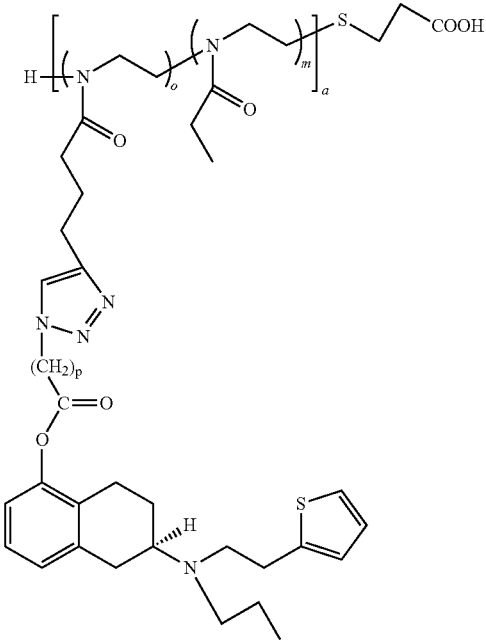

Linking Group

In the embodiments described above, the agent is linked to the poly(oxazoline) polymer by a releasable, hydrolyzable linkage. The releasable, hydrolyzable linkage contains a hydrolyzable moiety allowing the linkage to be cleaved after administration of the poly(oxazoline) polymer conjugate to a subject. The releasable, hydrolyzable linkage may contain portions of the polymer and/or portions of the agent as such portions have reacted to form the linkages required to form the poly(oxazoline) polymer conjugate as discussed herein.

Exemplary hydrolyzable moieties include, but are not limited to, carboxylate esters (—C(O)—O—), carbonate esters (—O—C(O)—O—), carbamates (—O—C(O)—NH—), disulfides (—S—S—), sulfides (—S—), acetals (—CH(OR')(OR'')), hemiacetals (—CH(OR')(OH)), phosphates (—O—P(O)(OH)—(O)—), phosphonates (—O—P(O)(OR')—(O)—) and amides (—C(O)—NH—); other hydrolyzable moieties are discussed herein. In a particular embodiment, the hydrolyzable moiety is an ester. In addition, the releasable, hydrolyzable linkage may be a naturally occurring amino acid, a non-naturally occurring amino acid or a polymer containing one or more naturally occurring and/or non-naturally occurring amino acids.

In one embodiment, the releasable, hydrolyzable linkage is a di-substituted triazole that contains a hydrolyzable moiety in one of the $R_3$ or $R_4$ groups. In a specific embodiment, the di-substituted triazole has the structure:

In another embodiment, the di-substituted triazole has the structure:

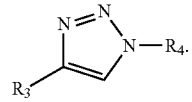

In each of the foregoing structures:
$R_3$ is a linker linking the triazole moiety to the polymer chain. $R_3$ is defined by the functional group on the polymer chain. In one embodiment, $R_3$ is —C(O)—$R_5$—, where $R_5$ is absent or is a substituted or unsubstituted alkyl from 1 to 10 carbons in length; and $R_4$ is —$R_6$—$R_7$—$R_8$—, where $R_6$ is a substituted or unsubstituted alkyl or substituted or unsubstituted aralkyl, $R_7$ is a group containing the hydrolyzable moiety or a portion of the hydrolyzable moiety and $R_8$ is absent or O, S, $CR_c$, or $NR_c$, where $R_c$ is H or substituted or unsubstituted alkyl. In one embodiment, $R_7$ and $R_8$ combined form the hydrolyzable moiety. In one embodiment of the foregoing, $R_6$ is a straight chain substituted or unsubstituted C1-C16 alkyl or a branched substituted or unsubstituted C1-C16 alkyl. In one embodiment, $R_7$ is —$R_a$—C(O)—$R_b$—, —$R_a$—O—C(O)—$R_b$—, —$R_a$—O—C(O)—$R_b$—, —$R_a$—CH(OH)—$R_b$—, —$R_a$—S—S—$R_b$—, —$R_a$—S—$R_b$—, —$R_a$—O—P(O)(OR$_{11}$)—$R_b$— (where $R_{11}$ is H or a substituted or unsubstituted C1-C5 alkyl), or —$R_a$—C(O)—$R_b$—, where $R_a$ and $R_b$ are each independently absent or substituted or unsubstituted alkyl. In another embodiment, $R_a$ and $R_b$ are each independently absent or a C1-C16 substituted or unsubstituted alkyl. In another embodiment, $R_a$ and $R_b$ are each independently absent or a C1-C5 substituted or unsubstituted alkyl. In another embodiment, $R_a$ and $R_b$ are each absent.

In a particular embodiment, $R_7$ is —$R_a$—C(O)—$R_b$—, —$R_a$—O—C(O)—$R_b$—, —$R_a$—CH(OH)—$R_b$— or —$R_a$—O—P(O)(OR$_{11}$)—$R_b$—, $R_a$ and $R_b$ are each absent and $R_8$ is O, $R_7$ is —$R_a$—O—C(O)—$R_b$— or —$R_a$—C(O)—$R_b$—, $R_a$ and $R_b$ are each absent and $R_8$ is NH, and $R_7$ is —$R_a$—S—$R_b$—, $R_a$ and $R_b$ are each absent and $R_8$ is absent.

In a particular embodiment, $R_3$ is —C(O)—(CH$_2$)$_3$ and $R_4$ is —CH$_2$—C(O)—O—, —CH$_2$—CH$_2$—C(O)—O— or —CH$_2$(CH$_3$)—C(O)—O—.

In another embodiment, the releasable, hydrolyzable linkage has the structure $R_9$—Y—$R_{10}$, where Y is a hydrolyzable moiety and $R_9$ and $R_{10}$ are each groups linking Y to the polymer conjugate and the agent, respectively. $R_9$ and $R_{10}$ may be the same of different. In one embodiment, $R_9$ and $R_{10}$ are each independently absent or substituted or unsubstituted alkyl. In another embodiment, $R_9$ and $R_{10}$ are each independently absent or a C1-C16 substituted or unsubstituted alkyl. In one embodiment, $R_9$ and $R_{10}$ are each absent.

In one embodiment of the foregoing, the linking group is —$R_9$—C(O)—O—$R_{10}$—, —$R_9$—O—C(O)—O—$R_{10}$—, —$R_9$—O—C(O)—NR$_{16}$—$R_{10}$— (where $R_{16}$ is a is H or a substituted or unsubstituted C1-C5 alkyl), —$R_9$—CH(OH)—O—$R_{10}$—, $R_9$—CH(OR$_{12}$)—O—$R_{10}$— (where $R_{12}$ is H or a substituted or unsubstituted C1-C5 alkyl), —$R_9$—S—S—$R_{10}$—, —$R_9$—S—$R_{10}$—, —$R_9$—O—P(O)(OR$_{12}$)—O—$R_{10}$— (where $R_{12}$ is H or a substituted or unsubstituted C1-C5 alkyl), —$R_9$—C(O)—NR$_{16}$—$R_{10}$— (where $R_{16}$ is a is H or a substituted or unsubstituted C1-C5 alkyl) or —$R_9$—[NR$_{16}$—CH(R$_{13}$)(R$_{14}$)—C(O)]$_q$—$R_{10}$— (where $R_{16}$ is a is H or a substituted or unsubstituted C1-C5 alkyl, $R_{13}$ is H or a C1-C5 alkyl, $R_{14}$ is a side chain group on a naturally occurring or non-naturally occurring amino acid and q is 1-10).

In one embodiment, the rate of cleavage of the hydrolyzable moiety is controlled by the nature of the releasable, hydrolyzable linkage. Additional control is provided by other parameters as discussed herein.

In each of the foregoing, the hydrolyzable moiety of the releasable, hydrolyzable linkage may be cleaved to release the agent. In one embodiment, the hydrolyzable moiety of the releasable, hydrolyzable linkage is cleaved chemically after administration to the subject under physiological conditions in the subject. In one embodiment, the hydrolyzable moiety of the releasable, hydrolyzable linkage is cleaved by a substance that is naturally present or induced to be present in the subject after administration to the subject under physiological conditions in the subject. In one embodiment, such substance is an enzyme or polypeptide. In one embodiment, the hydrolyzable moiety of the releasable, hydrolyzable linkage is cleaved by a combination of the foregoing.

Agent

The agent may be any agent useful in the treatment of a disease or condition or the diagnosis of a disease or condition. In certain embodiments, the agent is a diagnostic agent or a therapeutic agent. In certain embodiment, the therapeutic agent is an organic small molecule. Furthermore, the agent any molecule can be used having a therapeutic or diagnostic application, wherein the agent is capable of forming a linkage with a functional group on a POZ polymer or the releasable, hydrolyzable linker.

In one embodiment, the agent is useful for the treatment of PD or other diseases or conditions related to dopamine insufficiency in the peripheral or central nervous system. In one embodiment, the agent is useful for the treatment of PD. In such an embodiment, the agent may be a dopamine agonist.

Exemplary dopamine agonists include, but are not limited to, rotigotine, pramipexole, quinagolide, fenoldopam, apomorphine, 5-OH-DPAT, ropinirole, pergolide, cabergoline, and bromocriptine. In one embodiment, the dopamine agonist is rotigotine. In one embodiment, the dopamine agonist is (–)rotigotine. In one embodiment, the dopamine agonist is ropinirole.

PD is a central nervous system disorder resulting from loss of dopamine neurons in the substantia nigra pars compacta. The loss of these neurons in the brain leads to a deficiency of dopamine, a neurotransmitter that is essential for normal coordination and movement. Striatal dopaminergic neurons fire in a random, but continuous fashion due to stable levels of dopamine, allowing for precisely coordinated movements. In PD patients the pre-synaptic neurons degenerate. Administration of dopaminergic agents (dopamine agonists and levodopa) in an attempt to control symptoms leads to discontinuous stimulation of the post-synaptic neurons, promoting motor fluctuations that can worsen as the disease progresses (dyskinesias). Early symptoms of dopamine deficiency in PD include tremors, rigidity, bradykinesia, and gait problems. Cognitive and behavioral problems as well as dementia occur in later stages of PD.

While there is no cure for PD at this time, symptoms of this disease are treated with a variety of drugs aimed at maintaining dopaminergic tone. Drugs currently used for the treatment of PD include levodopa and dopamine agonists as well as other drugs. Levodopa is typically reserved for the later stages of PD while the other classes are the drugs of choice in the early stages of PD. There are challenges associated with these drugs. Levodopa can be administered orally, but gastrointestinal tract metabolism and erratic absorption limit bioavailability. For levodopa, bioavailability is less than 10% and even less reaches the brain intact due to peripheral metabolism, including metabolism by decarboxylase enzymes. To address this issue, decarboxylase inhibitors such as carbidopa are co-administered to inhibit peripheral metabolism. Furthermore, the short half-lives of these drugs require frequent dosing of several times daily which results in pulsatile stimulation of striatal dopamine receptors; this may actually accelerate the demise of dopaminergic neurons in the CNS. Low solubility of some of these compounds, with limited oral bioavailabity, further complicates their clinical use.

The use of dopamine agonists to treat PD is known in the art. The use of, 2-aminotetralins (a class of compounds with dopamine agonist activity) date back to the late 1980s in disclosures by Horn, A. S. (U.S. Pat. No. 4,722,933, February 1988 and U.S. Pat. No. 4,885,308, December 1989). Horn discussed analogues and small molecule pro-drugs of 2-aminotetralin to treat central nervous system disorders. One such example is rotigotine, a potent dopamine agonist. However, administration of rotigotine has proven to be difficult due to poor solubility in aqueous medium and short half-life. Swart and de Zeeuw report that oral and intraperitoneal bioavailability of rotigotine in rats to be less than 10% (Pharmacokinetics of the dopamine D2 agonist S(–)-2-(N-propyl-N-2-thienylethylamino)-5-hydroxytetralin in freely moving rats. J. Pharm. Sci. 1993 February; 82(2):200-3). Studies in man show that rotigotine has a half-life of 2.5 hours and it is rapidly metabolized to the sulfate and glucuronide analogues at the phenolic group. In an effort to improve the characteristics and oral bioavailability of these dopamine agonists, Stefano, Sozio, and Cerasa (Molecules 2008, 13: 46-68) prepared acetyl, propionyl, isobutyryl and carbamate pro-drugs. Esters of this type, however, would not be expected to improve water solubility and the improvement in duration in action was marginally increased from 3 to 4 hours to 11 to 15 hours. A transdermal patch was developed to address the suboptimal pharmacokinetics. This approach allows for 24 hours of delivery and improved bioavailability, but stability issues relating to poor solubility and crystallization in the patch resulted in this product's withdrawal from the U.S. market until formulation issues were addressed.

Ropinirole is another non-ergoline dopamine agonist that is delivered orally and has a half-life of 3 to 6 hours in man. Higher doses are required to achieve clinical benefit due to hepatic and renal metabolism. In addition, the once-a-day tablet dose generates undesired peak and troughs in blood concentration.

Therefore, there is a need in the art for new compositions for the treatment of PD and diseases or conditions related to dopamine insufficiency in the peripheral or central nervous system and diseases. The present disclosure provides polymer conjugates containing a poly(oxazoline) polymer and an agent useful in the treatment of PD, diseases or conditions related to dopamine insufficiency in the peripheral or central nervous system. The foregoing disorders will benefit from a polymer approach for sustained pharmacokinetics, increased bioavailability and ease of administration.

The polymer conjugates of the present disclosure have been exemplified by POZ-rotigotine and POZ-ropinirole.

Other agents, including those disclosed herein, are also useful in the conjugates of the present disclosure.

Dopamine Agonists

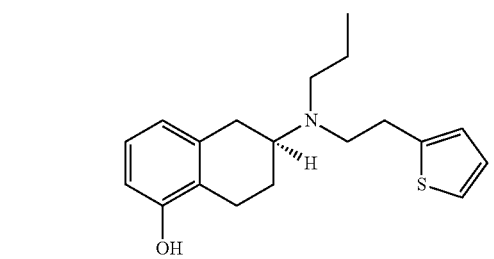

Rotigotine

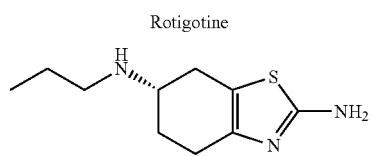

Pramipexole

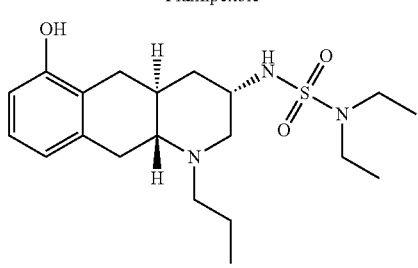

Quinagolide

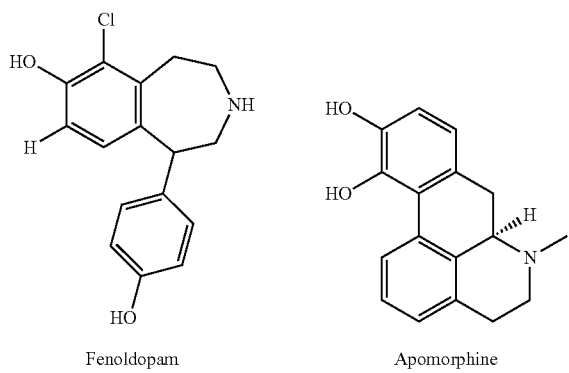

Fenoldopam          Apomorphine

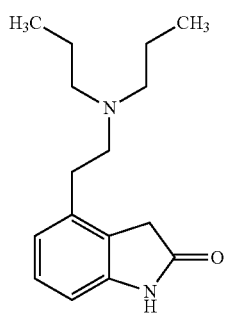

Ropinerole

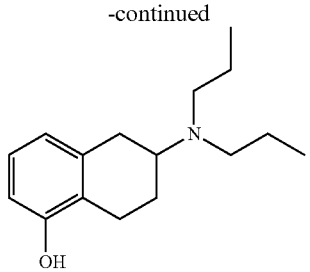

5-OH-DPAT

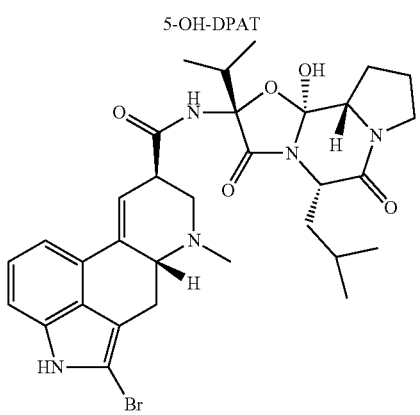

Bromocriptine

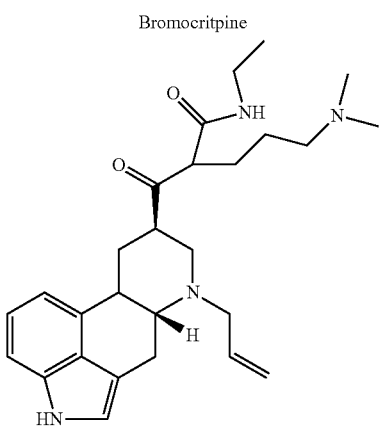

Cabergoline

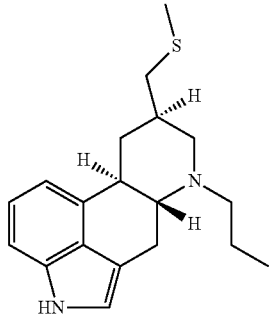

Perigolide

For clarity, the agent may be any of the dopamine agonists discussed herein or other dopamine agonists that have appropriate chemical functionality to form a linkage with a poly (oxazoline) polymer or releasable, hydrolyzable linker of the present disclosure. The exemplary compounds are presented by way of exemplification and are not intended to be limiting.

Furthermore, the agent may be used to treat a variety of diseases or conditions. The present specification described certain agents useful for the treatment of PD, diseases and conditions related to dopamine insufficiency in the peripheral or central nervous system. The foregoing examples are presented by way of exemplification and are not intended to be limiting.

Control of Release of Agent

The present disclosure provides poly(oxazoline) polymer conjugates where the release kinetics of the agent from the poly(oxazoline) polymer can be controlled by varying one or more parameters of the poly(oxazoline) polymer conjugate or route of administration. Such parameters include, but are not limited to, the nature of the linking group, the dose of the polymer conjugate administered, the size of the polymer, and the mode of administration. Table 1 provides experimental data on control of hydrolysis rates of the agent from the poly(oxazoline) polymer by varying the nature of the parameters of the poly(oxazoline) polymer conjugate.

As discussed above, the release kinetics of the agent from the poly(oxazoline) polymer conjugate (i.e., the rate of cleavage of the releasable, hydrolyzable linker) is controlled, in one embodiment, by the nature of the linking group. For example, as shown in Table 1 for hydrolysis of polymer-triazine-alkyl-$CO_2$-rotigotine, changes in the alkyl group affect the hydrolytic release of the agent rotigotine. Furthermore, Table I shows that the nature of the polymer affect the hydrolytic release of the agent rotigotine. POZ polymers provided a slower release of the agent while PEG and dextran polymers provided a rapid (less than 15 minute half life) release of the agent. Slower release of the agent avoids a rapid spike in agent concentration in the blood followed by rapid clearance. Such a profile results in sustained release of the agent over time. In some instances a single administration of a poly(oxazoline) polymer conjugate of the present disclosure can provide for therapeutically effective concentrations of the agent in the blood over a period of several days to weeks.

In addition, the size of the polymer contained in the poly(oxazoline) polymer conjugate impacts the rate of release of the agent into systemic circulation. For example, with subcutaneous administration, the rate of release of the poly(oxazoline) polymer conjugate from the subcutaneous compartment is controlled, at least in part, by the size of the poly(oxazoline) polymer. As polymer size increases, the rate of systemic clearance from the subcutaneous compartment decreases. As polymer size decreases, the rate of systemic clearance from the subcutaneous compartment increases. As a result, the entrance of the polymer into the systemic circulation, and subsequent cleavage of the releasable, hydrolyzable linker to release the agent, can be controlled.

Furthermore, the route of administration affects the rate of release of the agent into the systemic circulation. Administration by the subcutaneous route results in a slower and sustained release of the agent into the systemic circulation compared to other routes of administration, such as for example, intravenous administration. Administration via the intravenous route results in a more rapid release of the agent into the systemic circulation. These concepts are illustrated in Example 29 and FIGS. 2 and 3 for rats. Example 30 shows similar results for pharmacokinetics in monkeys, and Example 31 shows similar results for pharmacodynamics for rats.

Figure 2:
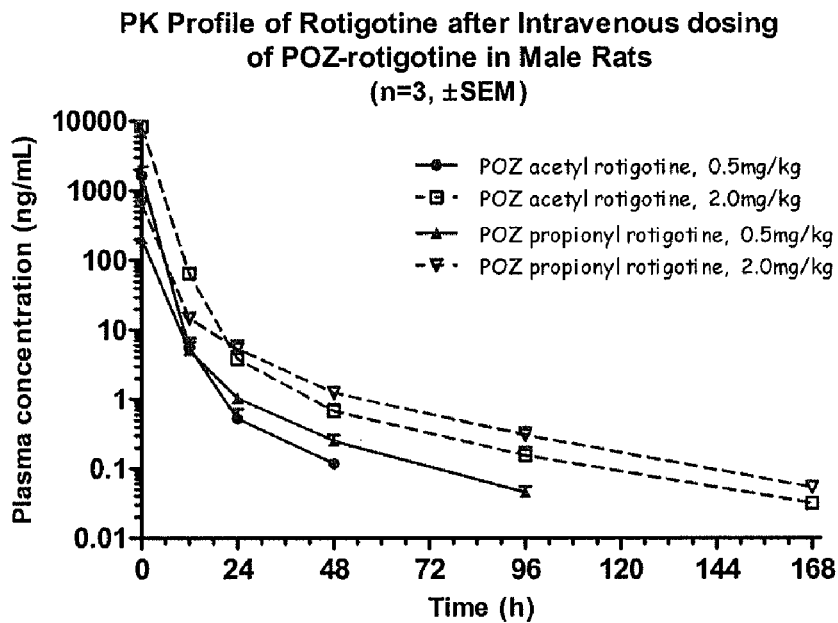
FIG. 2 shows the pharmacokinetic profile of rotigotine after intravenous dosing of POZ rotigotine in male Sprauge-Dawley rats.
Figure 3:
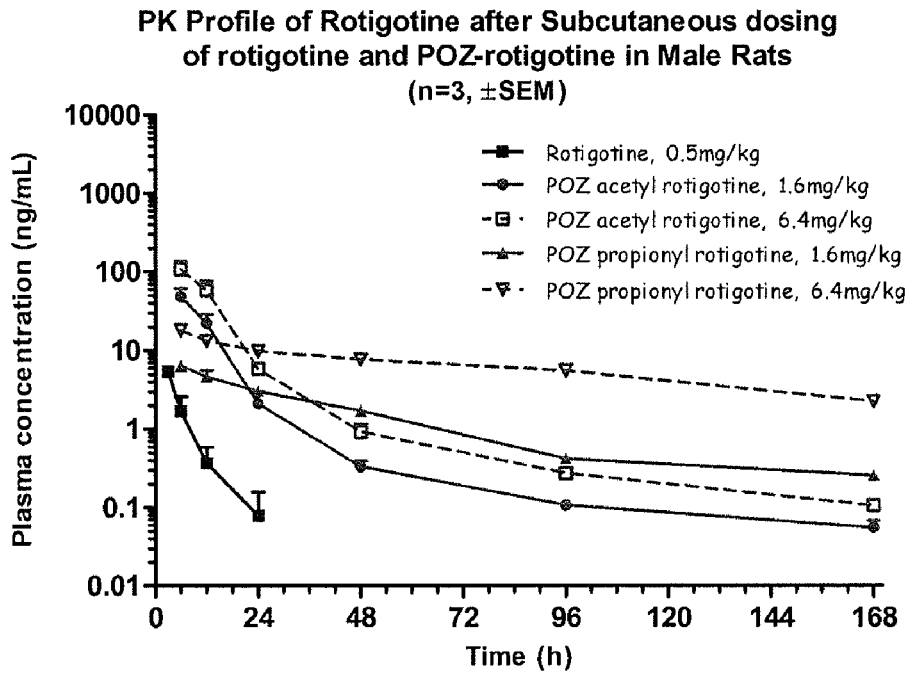
FIG. 3 shows the pharmacokinetic profile of rotigotine after subcutaneous dosing of POZ rotigotine in male Sprauge-Dawley rats.

The plasma concentration of rotigotine (ng/mL) after intravenous and subcutaneous injection of POZ-rotigotine is shown in FIGS. 2 and 3, respectively. These results show that use of POZ conjugates of rotigotine, whether dosed intravenously (IV) or subcutaneously (SC), will reduce the clearance rate of rotigotine from the blood when compared to the parent molecule alone. The terminal plasma half-life (t½) for rotigotine, POZ acetyl rotigotine and POZ propyl rotigotine was 2.8, 16 and 60 h, respectively. However, there is a striking difference in the PK profiles for the POZ-conjugates POZ acetyl rotigotine and POZ propyl rotigotine when route of administration is compared (IV vs SC). POZ-conjugates delivered IV are generally cleared in a bi-phasic pattern with little difference between POZ acetyl rotigotine and POZ propyl rotigotine. However, when POZ acetyl rotigotine and POZ propyl rotigotine are compared following SC administration there is a marked difference. POZ acetyl rotigotine has essentially the same PK profile when delivered either SC or IV. POZ propyl rotigotine has a markedly prolonged PK profile that is near "zero order" kinetics. The nature of the releasable, hydrolyzable linker plays a role in the release of the agent, in this case rotigotine, and the levels measured in rat plasma from day 1 to day 7 are higher for the propyl linker than the acetyl linker. The initial plasma concentrations of rotigotine during the first 12 hours are lower for POZ propyl rotigotine when compared to the POZ acetyl rotigotine conjugate. At 12 hours, the $C_{max}$ values of plasma rotigotine were 6 ng/mL for POZ propyl rotigotine versus for 48 ng/mL for the POZ acetyl rotigotine when dosed SC at the dose of 1.6 mg/kg.

These results show that controlled delivery of an agent can be "tuned" to release the agent with a desired release profile without an initial burst effect based on the nature of the linking group, the dose of the polymer conjugate administered, the size of the polymer, the method of administration (for example, subcutaneous vs. IV injection) or a combination of the foregoing.

Methods of Treatment

The present disclosure provides polymer conjugates comprising a poly(oxazoline) polymer and an agent, the agent linked to the poly(oxazoline) polymer by a releasable, hydrolyzable linker. The present disclosure further shows that the release of the agent from the poly(oxazoline) polymer conjugate can be controlled. In one aspect, a near steady state release of the agent from the poly(oxazoline) polymer conjugate is achieved over a period of time from days to weeks. In one embodiment, such a release profile provides a therapeutically effective concentration of the agent over such time period. As a result, the poly(oxazoline) polymer conjugates of the present disclosure are useful for treating a variety of conditions. Furthermore, the POZ polymer conjugates of the present disclosure allow for less frequent administration as compared to the prior art compounds to achieve therapeutically effective concentrations of the agent in a subject. In one embodiment, poly(oxazoline) polymer conjugates of the present disclosure are administered once a day, once every other day, once a week or at other desired intervals.

In one embodiment, a method of treating a disease state or condition is disclosed. Such method comprises the step of administering to the subject an amount of a poly(oxazoline) polymer conjugate of the present disclosure to a subject. In one embodiment, such disease state or condition is PD. In one embodiment, such disease state or condition is a disease or condition related to dopamine insufficiency in the peripheral or central nervous system. In such embodiments, any poly(oxazoline) polymer conjugate described herein may be used and the agent may be selected based on the disease or condition to be treated.

In one embodiment, the present disclosure provides a method of treating a disease state or condition related to dopamine insufficiency in the peripheral or central nervous system. Such method comprises the step of administering to the subject an amount of a poly(oxazoline) polymer conjugate of the present disclosure to a subject wherein the agent is a dopamine agonist.

In one embodiment, the disease or condition related to dopamine insufficiency is PD. Therefore, the present disclosure provides a method of treating PD. Such method comprises the step of administering to the subject an amount of a poly(oxazoline) polymer conjugate of the present disclosure to a subject wherein the agent is a dopamine agonist.

In one embodiment, the disease or condition related to dopamine insufficiency is restless leg syndrome. Therefore, the present disclosure provides a method of treating restless leg syndrome. Such method comprises the step of administering to the subject an amount of a poly(oxazoline) polymer conjugate of the present disclosure to a subject wherein the agent is a dopamine agonist.

Any polymer conjugate of the present disclosure may be used in the methods above. In a particular embodiment, the following polymer conjugates may be used in such methods of treatment.

In one embodiment, the polymer conjugate is a poly(oxazoline) polymer conjugate and the agent is a compound useful in the treatment of PD or another disease or condition related to dopamine insufficiency in the peripheral or central nervous system.

In one embodiment, the polymer conjugate is a poly(oxazoline) polymer conjugate and the agent is a dopamine agonist.

In one embodiment, the polymer conjugate is a poly(oxazoline) polymer conjugate and the agent is rotigotine, pramipexole, quinagolide, fenoldopam, apomorphine, 5-OH-DPAT, ropinirole, pergolide, cabergoline, or bromocriptine.

In one embodiment, the polymer conjugate is a poly(oxazoline) polymer conjugate and the agent is rotigotine or (−)rotigotine.

In one embodiment, the polymer conjugate is a poly(oxazoline) polymer conjugate and the agent is ropinirole.

In the methods described, the polymer conjugate may be administered alone or as a part of a pharmaceutical composition as described herein. In one embodiment, the subject is determined to be in need of such treatment. In a further embodiment, the polymer conjugate is administered in a therapeutically effective amount. In the methods disclosed herein, the subject may be a mammal. In certain embodiments, the subject is a human.

In one embodiment, the methods of treatment are accomplished by subcutaneous administration of the poly(oxazoline) polymer conjugates of the present disclosure or pharmaceutical compositions containing such poly(oxazoline) polymer conjugates.

In addition, in one embodiment, such poly(oxazoline) polymer conjugate is administered once a day. In another embodiment, such poly(oxazoline) polymer conjugate is administered once every other day. In still a further embodiment, such poly(oxazoline) polymer conjugate is administered every third day, every fourth day, every fifth day or every sixth day. In yet a further embodiment, such poly(oxazoline) polymer conjugate is administered once a week. Other dosing frequencies may also be used based on the nature of the polymer conjugate selected and the release kinetics of the agent.

The poly(oxazoline) polymer conjugates described herein can also be administered in combination with other therapeutic agents, for example, other agents that are useful for treatment of PD or any other condition recited herein. Accordingly, in one embodiment the present disclosure also provides a composition comprising a poly(oxazoline) polymer conjugate described herein, at least one other therapeutic agent, and a pharmaceutically acceptable diluent or carrier.

Kits

The present disclosure provides a kit comprising, consisting essentially of or consisting of a poly(oxazoline) polymer conjugate of the present disclosure, packaging material, and instructions for administering the foregoing to a subject for the treatment of PD or another disease or condition related to dopamine insufficiency in the peripheral or central nervous system.

The present disclosure provides a kit comprising, consisting essentially of or consisting of a polymer conjugate of the present disclosure, at least one other therapeutic agent, packaging material, and instructions for administering the foregoing to a subject for the treatment of PD or another disease or condition related to dopamine insufficiency in the peripheral or central nervous system.

Methods of Manufacture

In one embodiment, the agent is linked to the poly(oxazoline) polymer using click chemistry. The click chemistry approach involves the reaction between an alkyne group and an azido group. In one aspect, the click chemistry reaction involves the reaction of an azidoester on the agent and an alkyne on the poly(oxazoline) polymer. In a particular embodiment of this aspect, the azidoester group is formed by suitable chemical reactions with a chemical group on the agent, such as, but not limited to, a hydroxyl group. An exemplary reaction would be the preparation of an azidoester by displacing a halide from a halo acid with sodium azide to form the azidoacid followed by esterification of the azidoacid with a hydroxyl group on the agent (exemplified here as rotigotine).

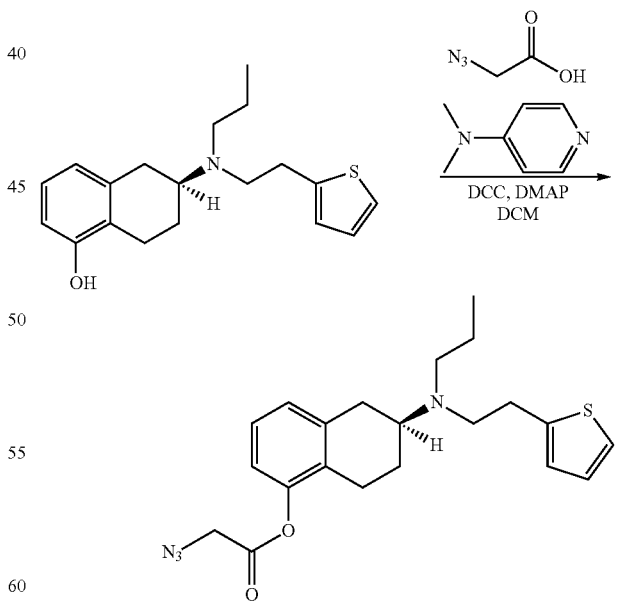

The azidorotigotine ester is then linked to an alkyne functionality present on the poly(oxazoline) polymer. In a particular embodiment, the alkyne functionality is an acetylene functionality present at a pendent position on the poly(oxazoline) polymer.

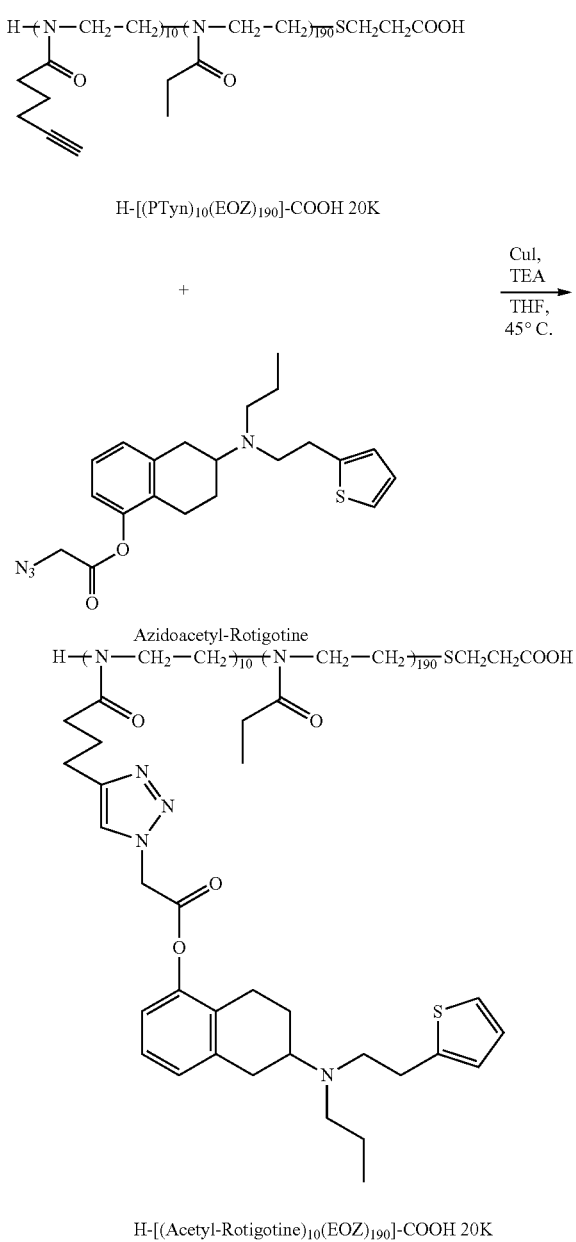

While the above method may be used, other approaches to the formation of hydrolyzable moieties may be used. For example, a linkage containing an ester hydrolyzable moiety may also be formed by creating an azide functional group on the poly(oxazoline) polymer, such as a pendent group on the poly(oxazoline) polymer, creating an alkyne group on the agent, such as an acetylene ester of rotigotine, and reacting the azide group and the alkyne group to form a releasable, hydrolyzable linkage containing a hydrolyzable moiety (in this case an ester bond).

In another approach, a carboxylic acid group can be created on the poly(oxazoline) polymer, such as a pendent group on the poly(oxazoline) polymer, and reacting the carboxylic acid group by directly esterifying an alcohol or phenolic group on the agent (for example rotigotine) to form a releasable, hydrolyzable linkage containing a hydrolyzable moiety (in this case an ester bond). In one embodiment, a carboxylic acid group on the poly(oxazoline) polymer is generated at a pendent position on the poly(oxazoline) polymer by including a carboxylated monomer in the polymerization reaction.

In the preparation of the poly(oxazoline) polymer conjugates of the present disclosure, the number of agents on the poly(oxazoline) polymer is controlled by the number of reactive groups present on the poly(oxazoline) polymer; in one embodiment, the reactive groups are present in a pendent position on the poly(oxazoline) polymer. For reactive groups at the pendent position, the number of reactive groups present on the polymer is controlled by the ratio of monomer units (for example, monomer oxazolines) having functionalized side chains (for example, acetylenes) capable of forming linkages with the agent or linking group relative to monomer units having inactive side-chains (for example, alkyls) used in the polymerization. In addition, for a given ratio of monomer units having functionalized side chains, the polymer length can be controlled providing further control of the number of agents loaded onto a given polymer conjugate. Therefore, the number of agents attached to a particular polymer conjugate can be controlled. As described above, the nature of the linking group, the size of the polymer and the route of administration allows control over the release kinetics of the agent from the polymer. These combined properties allow one to "tune" the release of the attached agent by varying the amount of agent delivered and varying the release kinetics of the agent for the desired pharmacology.

Pharmaceutical Compositions

Poly(oxazoline) polymer conjugates of the present disclosure can be formulated for both human and veterinary use. These formulations contain pharmaceutically accepted ingredients that act as fillers, binders, carriers, stabilizers, buffers, solvents, co-solvents, viscosity enhancers, lubricants, surfactants, flavoring and sweetening agents, taste-masking agents, inorganic salts, antioxidants, antimicrobial agents, chelating agents, lipids, phospholipids, (Ref: Handbook of Pharmaceutical Excipients, $3^{rd}$ edition, Ed. A. H. Kibbe, Pharmaceutical Press, 2000). The amount of agent in these formulations will depend on their physicochemical properties, dose and mode of administration. Most dosage forms will generally contain 1 to 99% by weight of the total formulation.

Formulations suitable for oral administration can be in solid form and they include tablets, pills, capsules, cachets, lozenges, fast dissolving solids, fine powders and granular powders. A tablet is a compression or mold of the drug conjugate and acceptable pharmaceutical excipients. Capsules are gelatin and non-gelatin cachets that encapsulate the drug and excipients. Formulations are also in liquid form and they include solutions, suspensions, emulsions, syrups and elixirs. These liquids may be aqueous, sugar based and non-aqueous based, glycol based.

Formulations suitable for parenteral use are sterile liquids and sterile powders and lyophilized powders ready for reconstitution in a suitable aqueous medium. Examples of the latter are sterile water for injection, 5% dextrose solution for injection, and 0.9% sodium chloride solution for injection, and lactated Ringer's injection. These formulations can be administered intravenously, subcutaneously, intramuscularly, and intradermally. These formulations are pH balanced and isotonic to blood and surrounding tissue. Similar formulations can be delivered as nasal sprays and eye drops.

Topical, transdermal and rectal formulations are water, polymer and oil based. They can be dissolved or suspended in mineral oil, petroleum waxes, liquid and solid polyols, polyhydroxy alcohols, cocoa butter, hydrogenated fats, surfactants, and esters of carboxylic acids. Transdermal formulations are reservoir or monolithic in design and the drug conjugates are typically in soluble form.

EXPERIMENTAL EXAMPLES

Example 1

Synthesis of random H-[(Ptyn)$_{10}$(EOZ)$_{190}$]-CO$_2$H

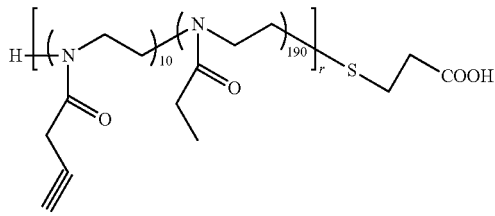

The synthesis of POZ polymers with various pendent groups is described in U.S. Pat. Nos. 8,110,651 and 8,101,706, each of which is incorporated herein by reference for such teachings. In a specific embodiment, the synthesis of H—[(Ptyn)$_{10}$(EOZ)$_{190}$]-T-CO$_2$H is provided although other POZ polymers with different molecular weights, different initiating and terminating groups as well as different pendent groups may be produced by the same methods. In addition, block copolymers may be produced in addition to random copolymers. Methods for producing random and block copolymers are described in U.S. Pat. Nos. 8,110,651 and 8,101,706, each of which is incorporated herein by reference for such teachings.

For the synthesis of H—[(Ptyn)$_{10}$(EOZ)$_{190}$]-CO$_2$H, triflic acid (HOTf, 173.3 µL, 1.96 mmol) was added to a solution of 2-pentynyl-2-oxazoline (PtynOZ, 3.76 g, 27.4 mmol, 14 eq) and 2-ethyl-2-oxazoline (EOZ, 46.61 g, 470.2 mmol, 240 eq) in chlorobenzene (124 mL). After stirring for 5 minutes at room temperature, the mixture was heated to 80° C. for 10 hours followed by cooling to room temperature. In a separate flask, the terminating reagent was prepared by the drop by drop addition of methyl 3-mercaptopropionate (1.23 mL, 0.0114 mol) into a suspension of sodium hydride (60% in mineral oil, 0.272 g, 0.0068 mol) in chlorobenzene (34 mL). This mixture was stirred for 7 hours, before the solution of living polymer of H-(Ptyn)$_{10}$(EOZ)$_{190}$$^+$ was added. The resulting mixture was then stirred for 18 hours. The solvent was removed by rotary evaporation to yield a white residue. This residue was dissolved in water and the pH adjusted to 12.0. The resulting aqueous solution was purified by ion-exchange chromatography using DEAE Sepharose FF. The aqueous solution was saturated with NaCl (15% w/w) and extracted with dichloromethane. The combined organic phases were dried over anhydrous sodium sulfate, filtered, and concentrated using a rotary evaporator. The residue was precipitated by adding the dichloromethane concentrate to diethyl ether. The precipitated material was collected and dried in vacuo to give 22.8 g of desired product as a white powder (50% yield).

$^1$H NMR (Varian, 500 MHz, 10 mg/mL CDCl$_3$) showed the usual backbone peaks at 1.13 ppm (m, 3H, CH$_3$CH$_2$CO—); 2.32 ppm (m) and 2.41 (s) (total area 2H, CH$_3$CH$_2$CO—); and 3.47 ppm (m, 4H, —NCH$_2$CH$_2$N—). The terminal group peaks appear at 2.63 ppm (m, 2H, —SCH$_2$CH$_2$CO$_2$H), 2.74 ppm (m, 2H, —CH$_2$SCH$_2$CH$_2$CO$_2$H), and 2.85 ppm (m, 2H, —SCH$_2$CH$_2$CO$_2$H). The pendent pentynyl group peaks appear at 1.85 ppm (m, 2H, —CH$_2$CH$_2$C≡CH) and 2.03 ppm (br s, 1H, —CH$_2$CH$_2$C≡CH). The number of pendent, Ptyn, groups were determined as 8.5 by comparing the integrations of terminal acetylene proton and polymer backbone protons. GPC gave Mn=19,500 Da and Mp=20,800 Da with PDI of 1.07.

Example 2

Synthesis of Azidoacetic Acid in Non-Aqueous Solvents

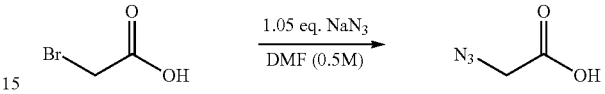

This example provides a general synthetic scheme for the synthesis of various azidoalkyl acid linkers. To exemplify this method, the synthesis of 2-azidoacetic acid is provided. Through the substitution of 2-bromoacetic acid, used in the synthesis of 2-azidoacetic acid, with other reagents azidoalkyl acid linkers, such as, but not limited to, 3-azidopropionic acid and 2-azoidopropionic acid, may be produced.

To a solution of 2-bromoacetic acid (1 g, 7.20 mmol) in DMF (14.39 ml) was added sodium azide (0.491 g, 7.56 mmol). After stirring for 16 hours at room temperature, the reaction mixture was monitored by RP HPLC (98% conversion).

H$^1$ NMR analysis (10 mg/mL in CDCl$_3$) showed the relevant peak at 3.84 ppm (s, 2H, N$_3$CH$_2$CO$_2$H).

Example 3

Synthesis of Rotigotine-2-Azidoacetate

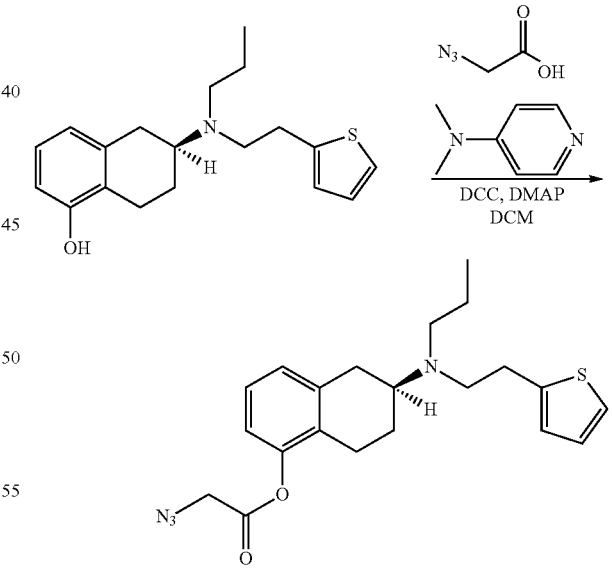

In a 25 mL round bottom flask, was placed rotigotine (1 g, 3.17 mmol, 1 equiv.), 2-azidoacetic acid-DMAP salt (0.849 g, 3.80 mmol, 1.2 equiv.) and 32 mL of anhydrous dichloromethane (DCM) and the mixture stirred under argon. DMAP (0.077 g, 0.634 mmol, 0.2 equiv.) and DCC (0.785 g, 3.80 mmol, 1.2 equiv.) were added as solids. The mixture was stirred for 16 hours at room temperature. The mixture was then filtered to remove precipitated urea and concentrated using a rotary evaporator. The crude mixture was first purified by silica gel column chromatography using a mixture of ethyl acetate and hexanes (1:2) as an eluent to give a clear yellow oil (1.27 g, 92% yield).

A second purification was performed by reversed phase chromatography to remove free rotigotine and other small molecule impurities. A sample solution for loading was prepared by dissolving crude product (350 mg) in 0.1% TFA in acetonitrile (4.05 mL), followed by addition of 1 N HCl (0.91 mL) and 0.1% TFA in water (4.04 mL). The sample solution was filtered through a 0.2 μm PTFE syringe filter, and then loaded to a Waters SunFire Prep C18 OBD 30/250 Column (from Waters) on an ÄKTA Purifier system equipped with an UV detector at 214 nm. 0.1% TFA in water (A) and 0.1% TFA in acetonitrile (B) were used as mobile phase. The column was then eluted isocratically with 40% of mobile phase B at flow rate of 20 mL/min. The fractions that contained pure product were collected and pooled. Acetonitrile in the pooled fraction was evaporated by rotary-evaporation. The remaining aqueous solution was extracted with DCM (3×50 mL), dried over anhydrous sodium sulfate and filtered, followed by evaporation of the DCM. The residue was dried in vacuum (293 mg, 83%).

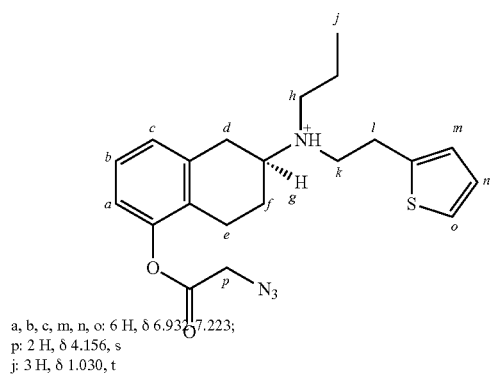

a, b, c, m, n, o: 6 H, δ 6.93-7.223;
p: 2 H, δ 4.156, s
j: 3 H, δ 1.030, t $^1$H NMR (Varian, 500 MHz, 10 mg/mL CDCl$_3$) showed peaks at 0.90 ppm (t, J=6.84 Hz, 3H), 1.25 (m, 1H), 1.29 (m, 1H), 1.49 (m, 1H), 1.59 (m, 1H), 2.05 (m, 2H), 2.54 (m, 3H), 2.82 (m, 3H), 2.97 (m, 3H), 4.156 N$_3$CH$_2$C(=O)O— (s, 2H), 6.81 (s, 1H), 6.88 (d, J=7.81 Hz, 1H), 6.92 (t, J=3.42 Hz, 1H), 7.02 (d, J=7.32 Hz, 1H), 7.13 (m, 2H).

Figure 1B:
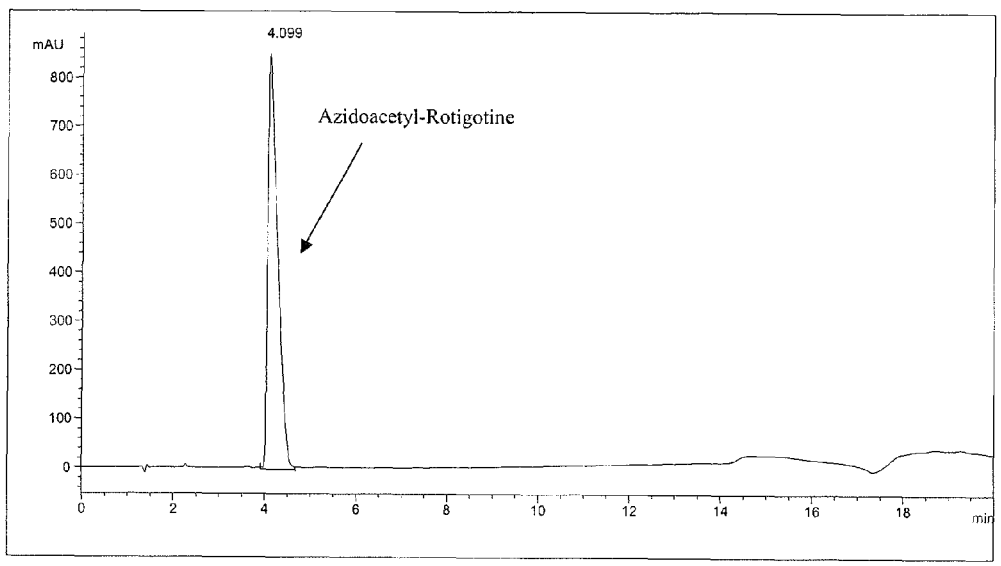
FIG. 1B shows an HPLC chromatogram of azidoacetyl-rotigotine after reversed phase chromatography purification

RP-HPLC analysis showed that the product contained no free rotigotine. The HPLC chromatogram of product before (FIG. 1A) and after (FIG. 1B) reversed phase chromatography purification are shown.

Example 4

Synthesis of Rotigotine-3-Azidopropionate

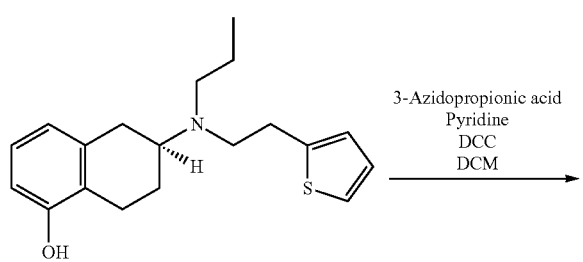

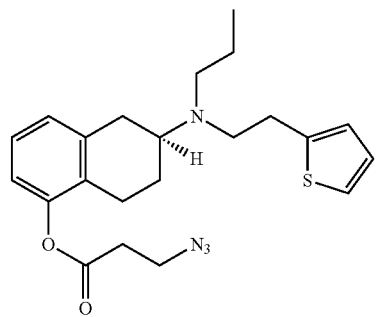

In a 50 mL round bottom flask, rotigotine (500 mg, 1.56 mmol, 1 equiv.), 3-azidopropionic acid (447 mg, 3.73 mmol, 2.4 equiv.—in 5 mL DCM), and pyridine (302 μL, 3.73 mmol, 2.4 equiv.) were dissolved in 50 mL anhydrous DCM and allowed to stir under argon. The solution was cooled in an ice-water bath for 5 min, and the bath was removed. To the solution DCC was added (778 mg, 3.73 mmol, 2.4 equiv.). The solution was allowed to stir at room temperature under argon. Following overnight reaction, reverse phase HPLC analysis of the reaction mixture showed complete conversion of free rotigotine to the ester form. The reaction mixture was filtered and the filtrate was concentrated to dryness on a rotary-evaporator. The crude product was then purified by silica gel chromatography. The crude product was dissolved in a mixed solvent of hexane-ethyl acetate (6 mL, 4:1 v/v) and then loaded onto a 300 mL silica gel column (30 mm id). The column was eluted with hexane-ethyl acetate (4:1 v/v). The fractions (10 mL each) were analyzed by TLC and reversed phase HPLC. The product fractions were pooled, evaporated by rotary-evaporation, and then dried under vacuum overnight. Yield: 292 mg.

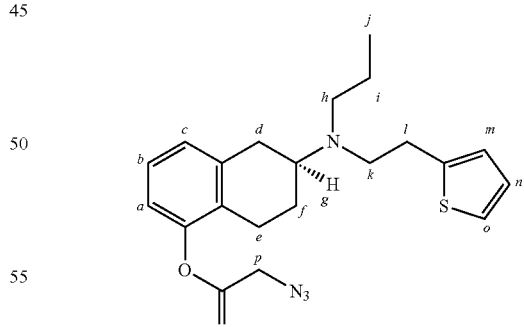

a, b, c, m, n, o: 6 H, δ 6.808-7.127;
p: 2 H, δ 2.838, t;
q: 2 H, δ 3.706, t;
j: 3 H, δ 0.895, t $^1$H NMR (Varian, 500 MHz, 10 mg/mL CDCl$_3$) showed peaks at 3.706 ppm N$_3$CH$_2$CH$_2$C(=O)O— (t, 2H) and 2.838 ppm N$_3$CH$_2$CH$_2$C(=O)O— (t, 2H).

Example 5

Synthesis of rotigotine-2-Azidopropionate

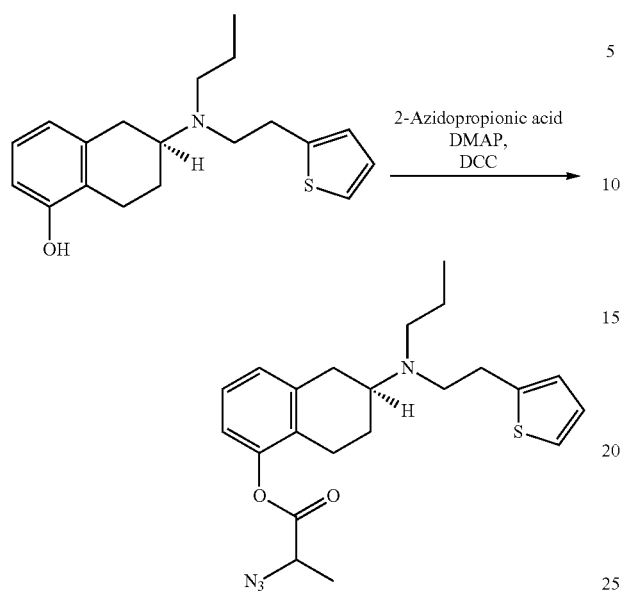

In a 100 mL round bottom flask was placed 2-azidopropionic acid (251 mg, 2.02 mmol, 1.3 equiv.—in 3 mL of DCM), rotigotine (500 mg, 1.55 mmol, 1 equiv.), and 4-DMAP (249 mg, 2.02 mmol, 1.3 equiv.—in 6 mL of DCM) and the mixture was allowed to stir under argon. The solution was cooled by placing the flask in an ice-water bath for 5 min. To the solution, DCC was added (421 mg, 2.02 mmol, 1.3 equiv.). The progress of the reaction was followed by reversed phase HPLC. Following overnight stirring at room temperature, additional 2-azidopropionic acid (126 mg, 0.65 equiv.) in 2 mL of DCM and 4-DMAP (124 mg, 0.65 equiv.) were added to the reaction mixture, followed by DCC (211 mg, 0.65 equiv.). The solution was allowed to stir at room temperature for another 3.5 hours. HPLC result shows 94% of conversion to ester. The reaction mixture was filtered, and the filtrate was concentrated to dryness on a rotary-evaporator. The crude product was then purified by silica gel chromatography. The crude product was dissolved in hexane-ethyl acetate (6 mL, 4:1 v/v), and then loaded on to a 300 mL Silica Gel Column (30 mm id). The column was eluted with a hexane-ethyl acetate (4:1 v/v). The fractions (10 mL each) were analyzed by TLC and reversed phase HPLC. The product fractions were pooled, evaporated by rotary-evaporation, and then dried in vacuum overnight. Yield: 307 mg.

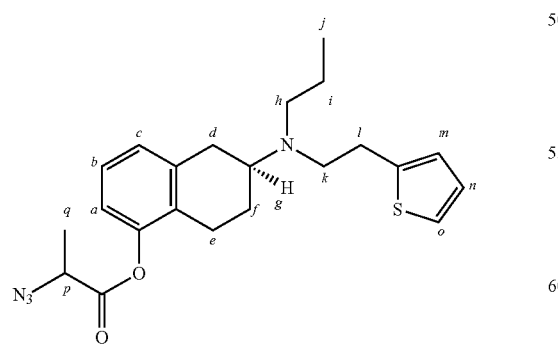

a, b, c, m, n, o: 6 H, δ 6.814-7.124;
p: 1 H, δ 4.203, q, ill resolved;
q: 3 H, δ 1.642, d;
j: 3 H, δ 0.896, t $^1$H NMR (Varian, 500 MHz, 10 mg/mL CDCl$_3$) showed peaks at 4.203 ppm CH$_3$CH(N$_3$)— (q, 1H) and 1.642 ppm CH$_3$CH(N$_3$)— (d, 3H).

Example 6

Preparation of H-[(Acetyl-Rotigotine)$_{10}$(EOZ)$_{190}$]-COOH 20K by attachment of Rotigotine Azidoacetate to Poly(oxazoline) 10 pendent acid

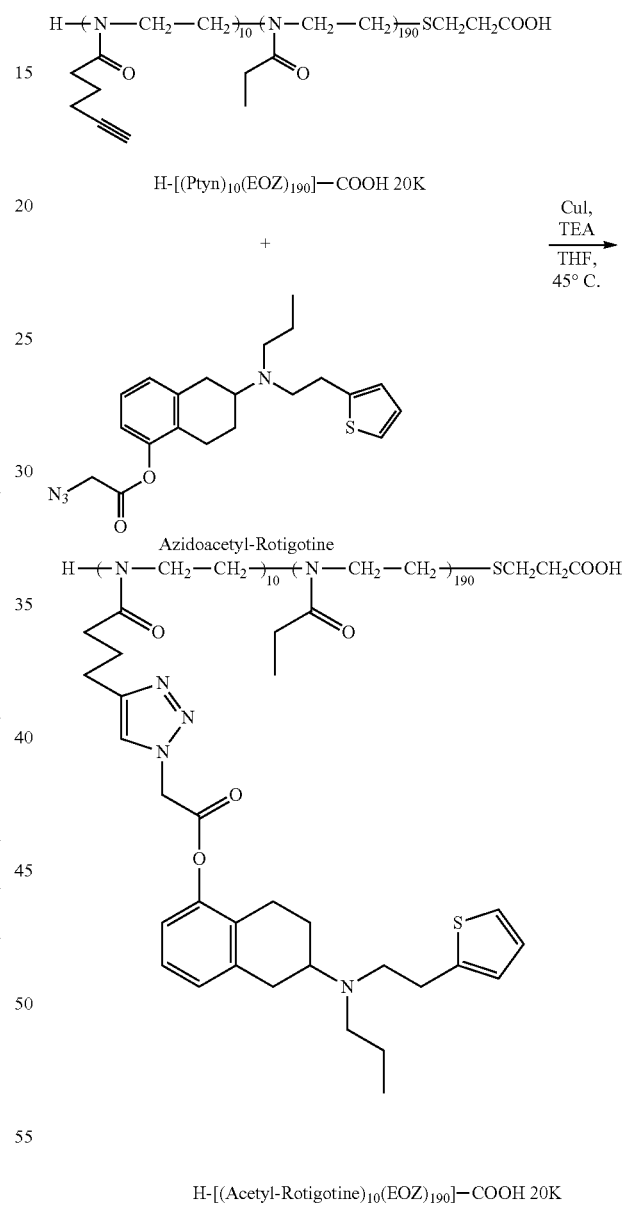

H-[(PtynOZ)$_{10}$(EOZ)$_{190}$]-COOH 20K polymer (1.306 g, 0.0653 mmol, 1.0 equiv.; Example 1) was dissolved in 15 mL of THF in a 100 mL round bottom flask. In a separate 50 mL round bottom flask, rotigotine azidoacetate (FW 384.50 Da, 251 mg, 0.653 mmol, 10.0 equiv.; Example 3) was dissolved in 15 mL of THF (15 mL). The rotigotine azidoacetate solution was transferred to the 100 mL round bottom flask. The solution was flushed with argon. Copper (I) iodide (≧99.5%, 50 mg, 0.261 mmol, 4.0 equiv.) was then added to the flask, followed by addition of TEA (127 μL, 0.914 mmol, 14.0 equiv.). The solution was allowed to stir overnight at 45° C. under argon. The green, crude reaction mixture was filtered with the aid of a 0.2 μm syringe filter, and then 0.1 N HCl (20 mL) was added to the filtrate. The mixture turned brown in color. The THF in the mixture was evaporated rotary evaporation at 28° C.

Two column purification steps were employed to purify the crude product. In step one, a glass column (2 cm ID) was packed with a slurry of silica gel 60 (EMD, 70-230 Mesh, 30 mL) in 60 mL of 0.1N HCl. Column packing and elution was done by gravity. Prewashed (water and 2 mM HCl acid) Dowex® M4195 media (20 mL) was packed above the silica layer. The column was equilibrated with 2 mM HCl (50 mL).

In a second glass column, Amberlite IR-120H (40 mL) was packed and washed with deionized water until the conductivity of the eluent was less than 1 μS/cm. The column was then equilibrated with 2 mM HCl (40 mL). The filtered crude reaction mixture (20 mL) which contained >300 mg/L $Cu^{+/2+}$ (measured by Quantofi Copper test stick), was loaded on to the first Dowex/silica gel column. The column was eluted with 2 mM HCl acid. The eluent that containing the H-[(Acetyl-Rotigotine)$_{10}$(EOZ)$_{190}$]-COOH 20K polymer (100 mL) was collected. The $Cu^+$/2+ level was less than 10 mg/L (Quantofi Copper test stick). Free rotigotine in the eluent was then removed by the Amberlite IR-120H as next described. The eluent of the Dowex/silica gel column (100 mL) was loaded onto Amberlite IR-120H (40 mL) column. The column was eluted with 1 mM HCl. To the eluent (150 mL) from the Amberlite column, NaCl was added to make 10% concentration. The cloudy solution was extracted with DCM (3×200 mL, gentle shaking) and dried over anhydrous sodium sulfate. The salt was filtered off, and the filtrate was concentrated to ~20 mL by rotary evaporation. The concentrated solution was added to 400 mL of ethyl ether to obtain a precipitate. Following filtration, the precipitate was dried under vacuum. The yield was 1.13 g. RP-HPLC analysis showed the absence of rotigotine and rotigotine azdioacetate. The product poly(oxazoline) conjugate of rotigotine was water soluble. The product had a rotigotine content of about 10% w/w.

$^1$H NMR (Varian, 500 MHz, 10 mg/mL CDCl$_3$) showed peaks at 5.479 ppm —NCH$_2$C(=O)O— (s, 2H), 6.945-7.197 from the phenyl and thiophene groups of rotigotine.

Example 7

Preparation of H-[(Propionyl-Rotigotine)$_{10}$(EOZ)$_{190}$]-COOH 20K by attachment of Rotigotine 3-Azidopropionate to Poly(oxazoline) 10 pendent acid 20K H-[(PtynOZ)$_{10}$(EOZ)$_{190}$]-COOH 20K (681 mg, 0.034 mmol, 1 equiv.; Example 1) was dissolved in 15 mL of THF in a 50 mL round bottom flask. In a 20 mL glass vial, rotigotine 3-azidopropionate (140 mg, 0.340 mmol, 10.0 equiv.; Example 4) was dissolved in 5 mL of THF. The rotigotine 3-azidopropionate solution was transferred into the 50 mL round bottom flask. The solution was flushed under argon. Copper (I) iodide, (≧99.5%, 26 mg, 0.136 mmol, 4.2 equiv.) was then added to the flask, followed by addition of TEA (20 μL, 0.144 mmol). The solution was allowed to stir overnight at 45° C. under an argon atmosphere. The green crude reaction mixture was cooled to room temperature and 0.1 N HCl (10 mL) was added to it. The reaction mixture became a clear yellow-brownish color. The THF in the mixture was evaporated by rotary evaporation at 28° C.

The reaction mixture was purified, extracted and precipitated as explained in Example 6. The yield was 611 mg. RP-HPLC analysis showed the absence of rotigotine and rotigotine 3-azidopropionate. The poly(oxazoline) conjugate of rotigotine was water soluble. The product had a rotigotine content of about 13% w/w.

$^1$H NMR (Varian, 500 MHz, 10 mg/mL CDCl$_3$) showed peaks at 4.829 ppm —NCH$_2$CH$_2$C(=O)O— (t, 2H), 6.876-7.194 from the phenyl and thiophene groups of rotigotine.

Example 8

Preparation of H-[(-[(α-Methyl-Acetyl-Rotigotine)$_{10}$(EOZ)$_{190}$]-COOH 20K by attachment of Rotigotine 2-Azidopropionate to Poly(oxazoline) 10 pendent acid 20K H-[(PtynOZ)$_{10}$(EOZ)$_{190}$]-COOH 20K (1.409 g, 0.070 mmol, 1 equiv.; Example 1) was dissolved in 15 mL of in a 100 mL round bottom flask. In a 20 mL glass vial, rotigotine 2-azidopropionate (291 mg, 0.705 mmol, 10.0 equiv.; Example 5) was dissolved in 15 mL of THF (15 mL). The rotigotine 2-azidopropionate solution was transferred into the 100 mL round bottom flask. The solution was flushed under argon. Copper (I) iodide (≧99.5%, 54 mg, 0.282 mmol, 4.0 equiv.) was then added to the flask, followed by addition of TEA (41 μL, 0.296 mmol, 4.2 equiv.). The solution was stirred overnight at 45° C. under an argon atmosphere. The reaction mixture was cooled to room temperature, filtered through a 0.2 μm PTFE syringe filter. 0.1 N HCl (20 mL) and added to the filtrate. The crude mixture turned clear brown. The THF in the mixture was evaporated by rotary evaporation at 28° C.

The reaction mixture was purified, extracted and precipitated as described in Example 6. The yield was 541 mg. RP-HPLC analysis showed the absence of rotigotine and rotigotine 2-azidopropionate. The product poly(oxazoline) conjugate of rotigotine was water soluble. The product had a rotigotine content of about 10% w/w. $^1$H NMR (Varian, 500 MHz, 10 mg/mL CDCl$_3$) showed peaks at 5.692 ppm —N(CH$_2$)CHC(=O)O— (s, H), 6.943-7.196 from the phenyl and thiophene groups of rotigotine.

Example 9

Preparation of H-[(N-Ropinirole)$_{10}$(EOZ)$_{190}$]-COOH 20K by attachment of Ropinirole 3-azidocarbamate to Polyoxazoline 10 pendent acid 20K

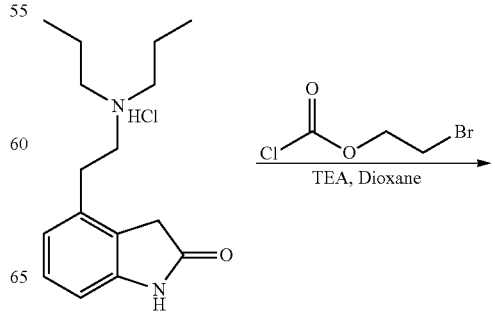

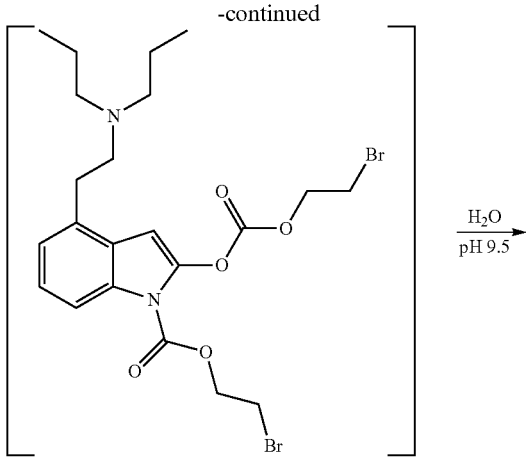

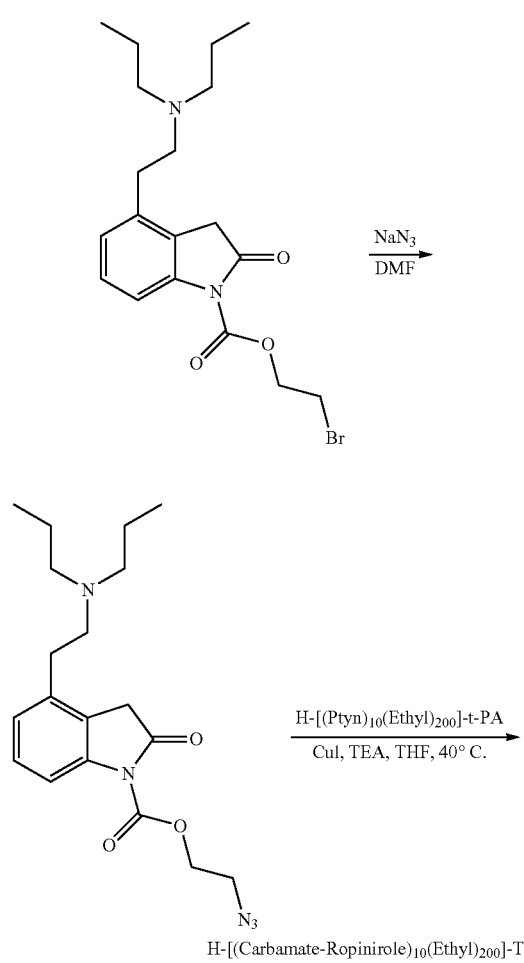

Ropinirole-N-bromoethylcarboxylate

To a solution of ropinerole ropinirole hydrochloride (0.558 g, 1.88 mmol) in dioxane (38 ml) was added triethylamine (2.10 ml, 15.1 mmol). After stirring for 5 minutes, 2-bromoethyl chloroformate (1.61 ml, 15.1 mmol) was added slowly and the mixture was allowed to stir overnight at room temperature. Water (40 mL) was added to give a mixture with pH of 9.5. After stirring overnight, the mixture was stirred with dichloromethane (40 mL) and brine solution (10 mL) for 10 minutes. The two layers were separated and the top layer was extracted with dichloromethane (40 mL). The combined organic phases were dried over $Na_2SO_4$, filtered, and concentrated to give dark red thick oil. Further purification was performed by silica gel column chromatography, eluting with dichloromethane/EtOAc (starting from 9:1, 4:1, and then 100% EtOAc) to give the desired N-acylated product as a dark red oil (0.170 g, 22.01% yield.). $^1$H NMR (Varian, 500 MHz, 10 mg/mL DMSO-$d_6$, δ): 0.83 (t, J=7.5 Hz, 6H, —$CH_2CH_2CH_3$), 1.39 (m, 4H, —$CH_2CH_2CH_3$), 2.39 (t, J=7.5 Hz, 4H, —$CH_2CH_2CH_3$), 2.62 (m, 4H, $Pr_2NCH_2CH_2$—Ar), 3.80 (s, 2H, —$CH_2C(=O)$—), 3.80 (t, J=5.5 Hz, 2H, —$OCH_2CH_2Br$), 4.65 (t, 2H, —$OCH_2CH_2Br$), 7.04 (d, J=8.0 Hz, 1H, Ar H), 7.25 (t, J=8.0 Hz, 1H, Ar H), 7.63 (d, J=8.0 Hz, 1H, Ar H).

Ropinirole-N-azidoethylcarboxylate

To a solution of Ropinirole-N-bromoethylcarboxylate (0.170 g, 0.414 mmol) in DMF (2 ml) was added sodium azide (0.027 g, 0.414 mmol) to give a clear yellow solution. After stirring overnight at room temperature, the mixture was quenched with 1 mL of 0.1 N HCl and then diluted with 2 mL of water. All the volatiles were removed using a rotary evaporator and the aqueous solution was extracted twice with dichloromethane (3 mL each). The combined organic phases were dried over $Na_2SO_4$, filtered, and concentrated to give Ropinirole-N-azidoethylcarboxylate (0.12 g, 78% yield) as thick yellow oil. $^1$H NMR (Varian, 500 MHz, 10 mg/mL DMSO-$d_6$, δ): 0.93 (t, J=Hz, 6H, —$CH_2CH_2CH_3$), 1.70 (m, 4H, —$CH_2CH_2CH_3$), 2.99 (m, J=Hz, 4H, $Pr_2NCH_2CH_2$—Ar), 3.07 (m, 4H, —$CH_2CH_2CH_3$), 3.22 (m, 4H, $Pr_2NCH_2CH_2$—Ar), 3.92 (s, 2H, —$CH_2C(=O)$—), 3.98 (t, 2H, —$OCH_2CH_2N_3$), 4.48 (t, 2H, —$OCH_2CH_2Br$), 7.14 (d, J=7.5 Hz, 1H, Ar H), 7.33 (t, J=8.0 Hz, 1H, Ar H), 7.69 (d, J=8.0 Hz, 1H, Ar H).

H-[(N-Ropinirole)$_{10}$(EOZ)$_{190}$]-COOH 20K

Ropinirole-N-azidoethylcarboxylate hydrochloride (0.12 g, 0.293 mmol) was dissolved in THF (15 ml). H-[(Ptyn)$_{10}$(Ethyl)$_{200}$]-T-PA (0.488 g, 0.024 mmol) was added and the mixture was stirred to form a solution. CuI (0.019 g, 0.098 mmol) and triethylamine (0.014 ml, 0.098 mmol) were added to give a clear red solution. After stirring for 16 hours at 45° C., the mixture was quenched with 2 mL of 0.1N HCl to give a solution with pH of 3. All the volatiles were removed and the residue was dissolved in methanol. The resulting mixture was passed through a Dowex and Amberlite IR-120 column using methanol as an eluent. After removing methanol, the resulting aqueous solution was extracted twice with dichloromethane (5 mL each). The organic solution was dried over $Na_2SO_4$, filtered, concentrated to 10 mL, and precipitated by adding into 70 mL of diethyl ether. The precipitate was filtered and dried in vacuo to give H-[(N-Ropinirole)$_{10}$(Ethyl)$_{200}$]-T-PA (0.50 g, 86% yield) as a pale yellow powder. In addition to the usual polymer backbone peaks, $^1$H NMR (Varian, 500 MHz, 10 mg/mL DMSO-$d_6$, δ) shows the polymer chain contained an average of 6.4 units of rotigotine with major Ropinirole peaks at 0.97 (m, 6H, —$CH_2CH_2CH_3$), 4.62 (m, 2H, —$OCH_2CH_2Br$ and m, 2H, —$OCH_2CH_2$-triazole ring), 7.19-7.39 (br m, 3H, Ar H), and 7.91 (m, 1H, triazole H).

Example 10

Coupling of 4-Arm Propargyl PEG (10K) to rotigotine 3-azidopropionate

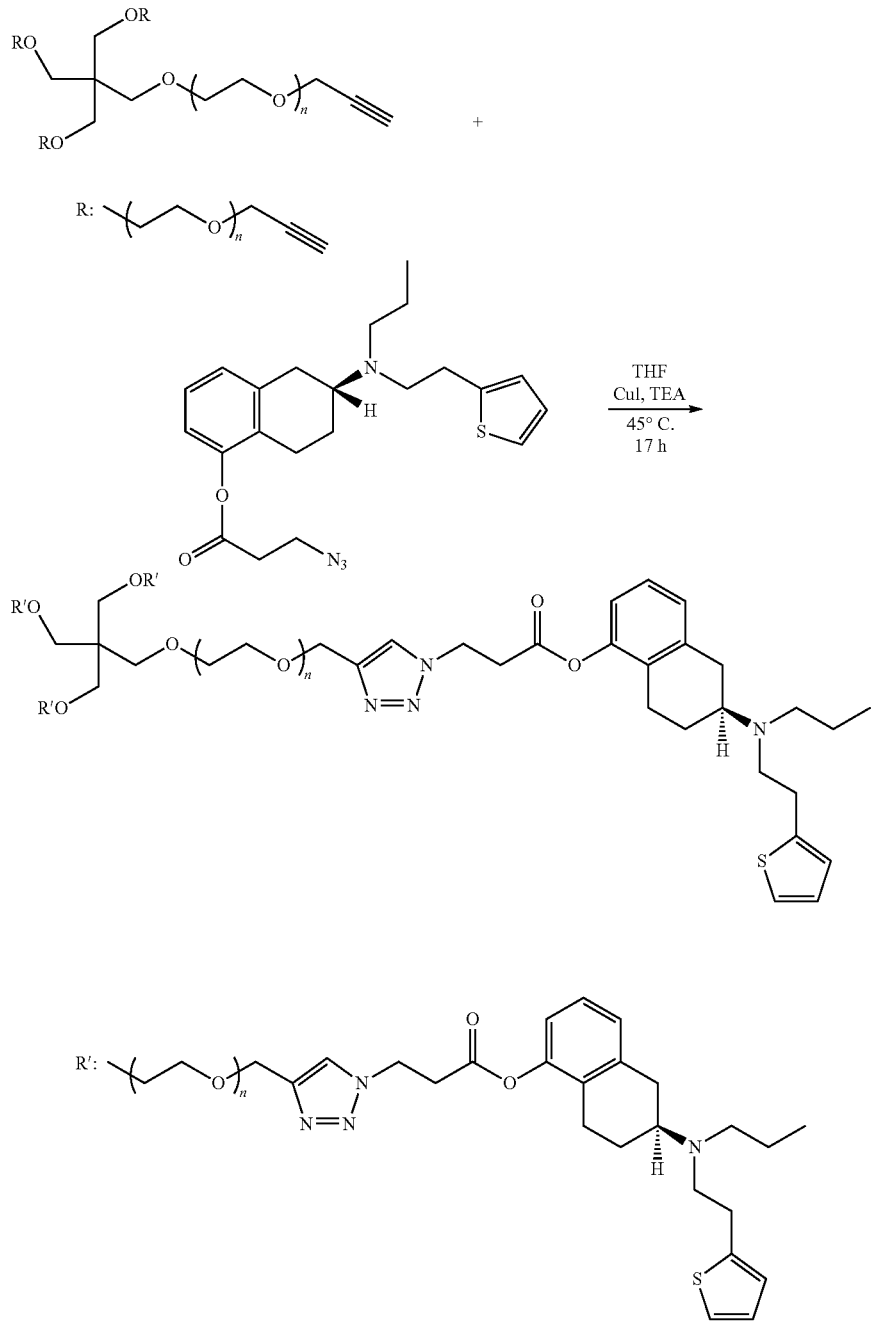

Rotigotine 3-azidopropionate TFA (95.0 mg 0.18 mmol) was dissolved in 20 mL of THF in a 50 mL one-neck round-bottom flask and 330 mg of 4-Arm propargyl PEG (Creative PEGWorks) (0.03 mmol, MW 11,000 Da) was added into the flask and the mixture was stirred to dissolve the polymer (brown mixture). Copper (I) iodide (9.3 mg, 0.048 mmol) and 6.63 µL of triethylamine (4.8 mg, 0.048 mmol) were added to give a clear brown solution. The solution was stirred at 45° C. under an argon blanket for 17 h. The brown mixture was cooled to room temperature and filtered through a 0.2 µM PTFE filter. The filtrate was stirred with 6 mL of 0.1 N HCl to give a brown mixture (pH 2.5 by pH paper). THF was removed by rotary evaporation at 28° C. The resulting cloudy aqueous solution was passed through a column packed with Dowex (10 mL, M4195, Supelco, 184426I) at the top and 20 g of Amberlite IR-120 (30 mL, Fluka, BCBF3074V) at the bottom, resulting in 200 mL of aqueous solution. The solution was saturated with 20 g of NaCl and extracted with 50 mL of DCM three times. The organic layers were separated, combined, dried over 20 g of $Na_2SO_4$, filtered, concentrated to 2 mL and precipitated by addition to 40 mL of diethylether in a 50 mL beaker. The polymer isolated by filtration and dried under vacuum to give 310 mg of the final product in 81% yield. The product had a rotigotine content of about 10% w/w.

$^1H$ NMR ($CDCl_3$, δ, ppm, TMS): 1.03 (3H, —$NCH_2CH_2CH_3$); 1.8-3.6 (total of 17H, aliphatic CH and $CH_2$ peaks of rotigotine; 2.56 (2H, —$OCOCH_2CH_2$-triazole); 3.41 (—$C(CH_2O)_4$); 3.64 (1000H, —$OCH_2CH_2O$—); 4.71 (2H, —$OCH_2$-triazole); 4.76 (2H, —$OCOCH_2CH_2$-triazole); 6.88-7.21 (6H, —CH peaks of 1,2,3,4-tetrahydronaphtalene and —CH peaks of 2-thiophene); 7.76 (1H, —CH peak of triazole).

Example 11

Coupling of 4-Arm Propargyl PEG (20K) to rotigotine 3-azidopropionate

Rotigotine 3-azidopropionate TFA (126.2 mg, 0.24 mmol) was dissolved in 40 ml of THF in a 50 one-neck round-bottom flask and 624 mg of 4-Arm Propargyl PEG (Creative PEG-Works, ZQ9216) (0.03 mmol, MW 20,800 Da) was added into the flask. The mixture was stirred to dissolve the polymer completely (yellow solution). Copper (I) iodide (9.63 mg 0.048 mmol) and 6.60 μL of triethylamine (4.8 mg, 0.048 mmol) were added to give a clear yellow solution. The resulting solution was stirred at 45° C. under argon for 40 h. The reaction was stopped after 40 h of stirring. The solution was filtered through a 045 μM PTFE filter. The filtrate was stirred with 12 mL of 0.1 N HCl resulting in a brown mixture (pH 2.5 by pH paper). THF was removed using by rotary evaporation at 28° C. The resulting cloudy aqueous solution was passed through a column packed with Dowex (20 mL, M4195, Supelco, 184426I) at the top and 40 g of Amberlite IR-120 (60 mL, Fluka, $BCBF_{3074}V$) at the bottom resulting in 400 mL of aqueous solution. The solution was saturated with 40 g of NaCl and extracted with 50 mL of DCM three times. The

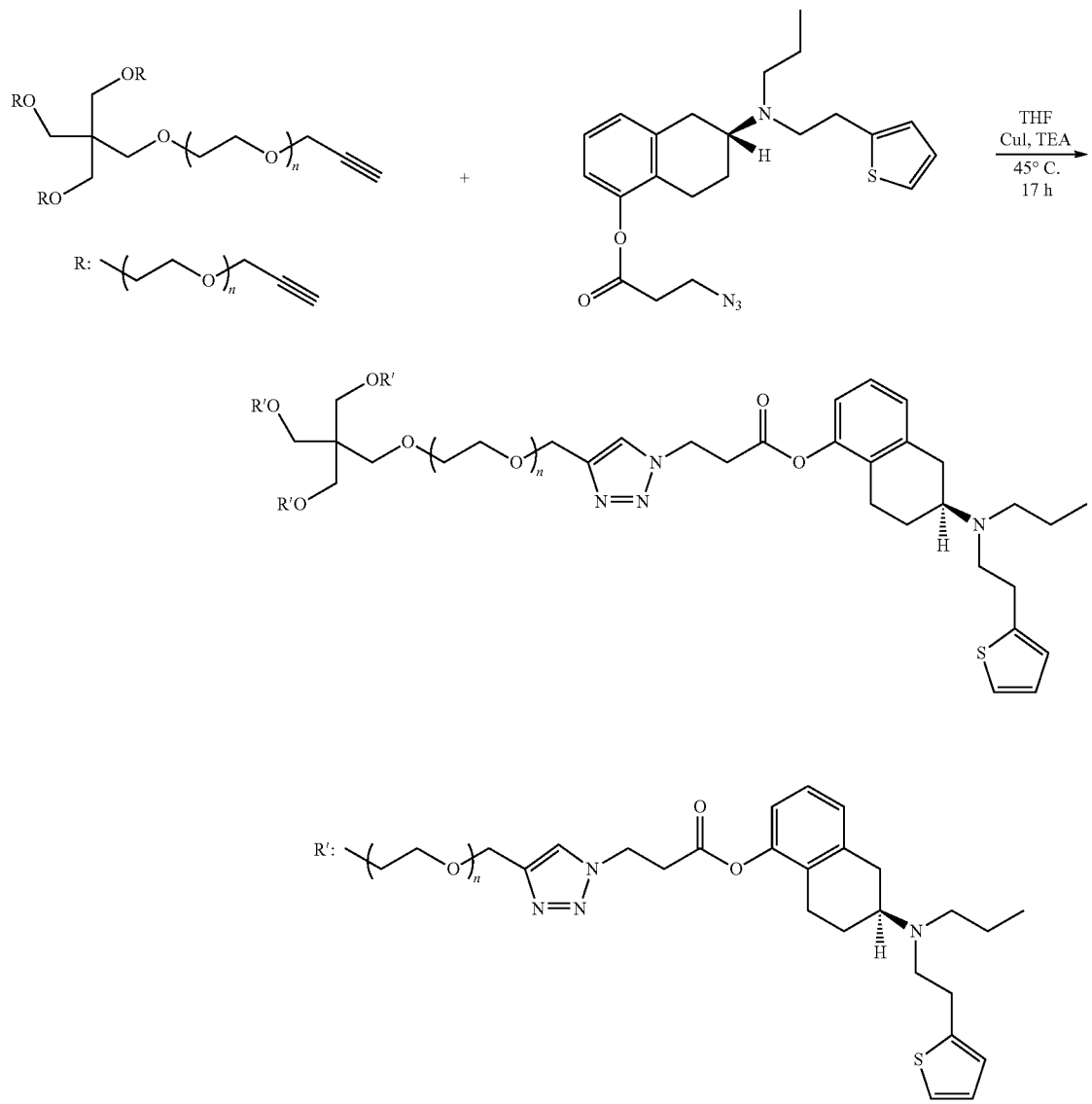

organic layers were separated, combined, dried over 20 g of Na$_2$SO$_4$, filtered and concentrated to 4 mL. The DCM solution was then precipitated into 80 mL of diethylether in a 100 mL beaker. The solvent was decanted and the polymer was dried under high vacuum to give 582 mg of the final product in 86% yield. The product had a rotigotine content of about 5% w/w.

$^1$H NMR (CDCl$_3$, δ, ppm, TMS): 1.03 (3H, —NCH$_2$CH$_2$CH$_3$); 1.8-3.6 (total of 17H, aliphatic CH and CH$_2$ peaks of rotigotine; 2.56 (2H, —OCOCH$_2$CH$_2$-triazole); 3.41 (2H, —C(CH$_2$O)$_4$); 3.64 (1000H, —OCH$_2$CH$_2$O—); 4.69 (2H, —OCH$_2$-triazole); 4.74 (2H, —OCOCH$_2$CH$_2$-triazole); 6.88-7.21 (6H, —CH peaks of 1,2,3,4-tetrahydronaphtalene and —CH peaks of 2-thiophene); 7.71 (1H, —CH peak of triazole).

Example 12

Synthesis of Polyethylene Glycol Dendrimer (26K)

The syntheses of PEG dendrimer was done in two steps. First the building of the PEG dendron blocks was completed and second the blocks were joined to create the dendrimer structure.

i. Preparation of Dendron Building Block:

organic phases were dried over Na$_2$SO$_4$, filtered, concentrated using a rotary evaporator, and dried in vacuo to give crude product as a waxy solid. The crude material was dissolved in water and passed through an Amberlite column and then an ion-exchange column using both DEAE Sepharose FF and SP Sepharose FF. The resulting aqueous solution was charged with NaCl (15% w/v) and extracted with dichloromethane. The combined organic phases were dried over anhydrous Na$_2$SO$_4$, filtered, concentrated using a rotary evaporator, and dried in vacuo to provide Et-G1-NHBoc (3.4 g, 84% yield). $^1$H NMR (Varian, 500 MHz, 10 mg/mL CDCl$_3$) showed the usual backbone peak at 3.64 ppm (m, 4H, —(OCH$_2$CH$_2$)$_n$—) and other major peaks at 1.28 ppm (t, 3H, —OCH$_2$CH$_3$), 1.44 ppm (s, 18H, —NHBoc), 4.01 ppm (m, 4H two protons for each PEG, —NHC(=O)CH$_2$—(OCH$_2$CH$_2$)$_n$—), 4.32 ppm (q, 2H, —OCH$_2$CH$_3$), 4.59 ppm (q, 1H, —CH(CO$_2$Et)NH—).

CO$_2$H-G1-NHBoc

Et-G1-NHBoc (0.975 g, 0.247 mmol) was dissolved in water (6.2 ml) and stirred overnight with 0.1 N NaOH (5 ml, 0.5 mmol). The mixture was acidified by adding 0.5 mL of 1N HCl, charged with 1.8 g of NaCl (15% w/v), and then stirred with 10 mL of DCM. The two layers were separated and the

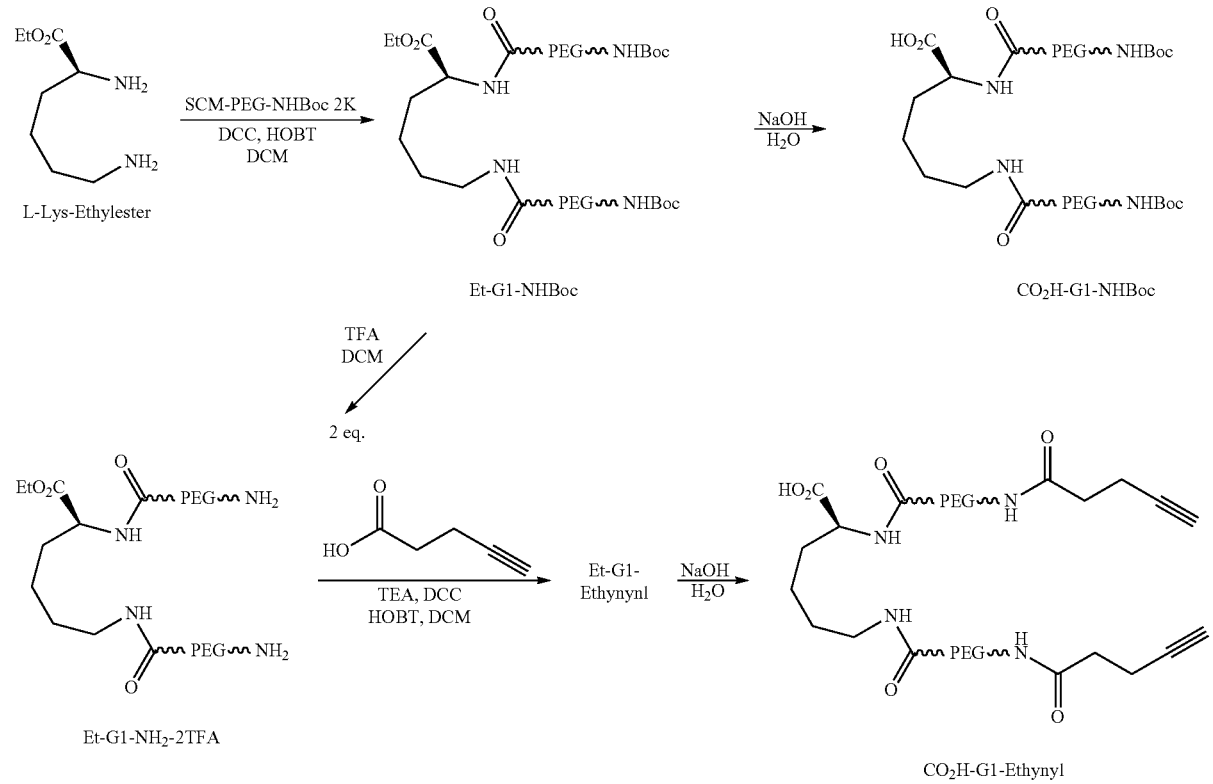

Et-G1-NHBoc.

L-lysine ethyl ester dihydrochloride (0.253 g, 1.025 mmol) and SCM-PEG-NHBoc 2K (4.71 g, 2.36 mmol) were dissolved in dichloromethane (170 ml). After addition of TEA (0.714 ml, 5.12 mmol), the mixture was stirred overnight at room temperature. The reaction mixture was quenched with 51 mL of 0.1N HCl solution and stirred with of NaCl (5.1 g). Two layers were separated and the aqueous phase was extracted with dichloromethane (50 mL). The combined aqueous phase was extracted with 8 mL of DCM. The combined organic phases were dried over Na$_2$SO$_4$, filtered, concentrated, and dried in vacuo to give CO$_2$H-G1-NHBoc (0.928 g, 96% yield) as a pale yellow waxy powder. The completion of the hydrolysis was confirmed by $^1$H NMR (Varian, 500 MHz, 10 mg/mL CDCl$_3$) revealed the disappearance of ester proton peaks, shown at 1.28 and 4.32 ppm (—OCH$_2$CH$_3$)

Et-G1-NH$_2$.2TFA

Et-G1-NHBoc (2.42 g, 0.613 mmol) was dissolved in dichloromethane (15.33 ml) and stirred with TFA (2.36 ml, 30.7 mmol) for 1 hour at room temperature. Most of the volatiles were removed using a rotary evaporator to give ~4.5 g of thick red extract. The crude product was stirred with 30 mL of diethyl ether to give a sticky powder and a slightly cloudy suspension. After decanting the liquid, the residue was stirred with 30 mL of diethyl ether. After decanting the solution, the pale white powder (waxy) was dried overnight in vacuo. The crude product was dissolved in 25 mL of dichloromethane and then washed with brine (20 mL), dried over Na$_2$SO$_4$, filtered, concentrated using a rotary evaporator, and dried in vacuo to give Et-G1-NH$_2$.2TFA (2.10 g, 86% yield). The completion of the deprotection was confirmed by the disappearance of -Boc group proton peak, shown at 1.44 ppm (s, 18H, —NHBoc).

CO$_2$H-G1-Ethynyl

HOBT (0.209 g, 1.362 mmol) was dried by azeotropic distillation using acetonitrile. To the residue was added a solution of 4-pentynoic acid (0.125 g, 1.277 mmol) in dichloromethane (20 ml). DCC (0.264 g, 1.277 mmol) was added and the mixture was stirred for 10 minutes to give a cloudy solution. A solution of Et-G1-NH$_2$.2TFA (1.69 g, 0.426 mmol) with TEA (0.356 ml, 2.55 mmol) in dichloromethane (20 ml) was added. After stirring for 18 hours, the reaction mixture was filtered using a syringe filter and quenched with 0.1N HCl. All the organic volatiles were removed using a rotary evaporator and passed through an Amberlite column and then an ion-exchange column using DEAE Sepharose FF. The resulting aqueous solution was charged with NaCl (15% w/v) and extracted with dichloromethane. The organic phase was dried over anhydrous Na$_2$SO$_4$, filtered, concentrated using a rotary evaporator, and dried in vacuo to provide Et-G1-Ethynyl.

Hydrolysis of Et-G1-Ethynyl

The ethyl ester product was dissolved in water and the pH of the solution was adjusted to 13 using 0.5 N NaOH. After stirring overnight, the mixture was acidified to pH 3 and purified on an Amberlite column and an ion-exchange column using DEAE Sepharose FF to give 1.14 g (69% yield) of CO$_2$H-G1-Ethynyl as the desired product. $^1$H NMR (Varian, 500 MHz, 10 mg/mL CDCl$_3$) showed the usual backbone peak at 3.64 ppm (m, 4H, —(OCH$_2$CH$_2$)$_n$—) and other major peaks at 2.03 (m, 2H, —CH$_2$CH$_2$CCH), 2.42 (t, 4H, —CH$_2$CH$_2$CCH), 2.53 (t, 4H, —CH$_2$CH$_2$CCH), 3.98-4.16 ppm (m, 4H two protons for each PEG, —NHC(=O)CH$_2$—(OCH$_2$CH$_2$)$_n$—), 4.62 ppm (q, 1H, —CH(CO$_2$Et)NH—).

ii. Construction of Dendrimer via a Convergent Pathway

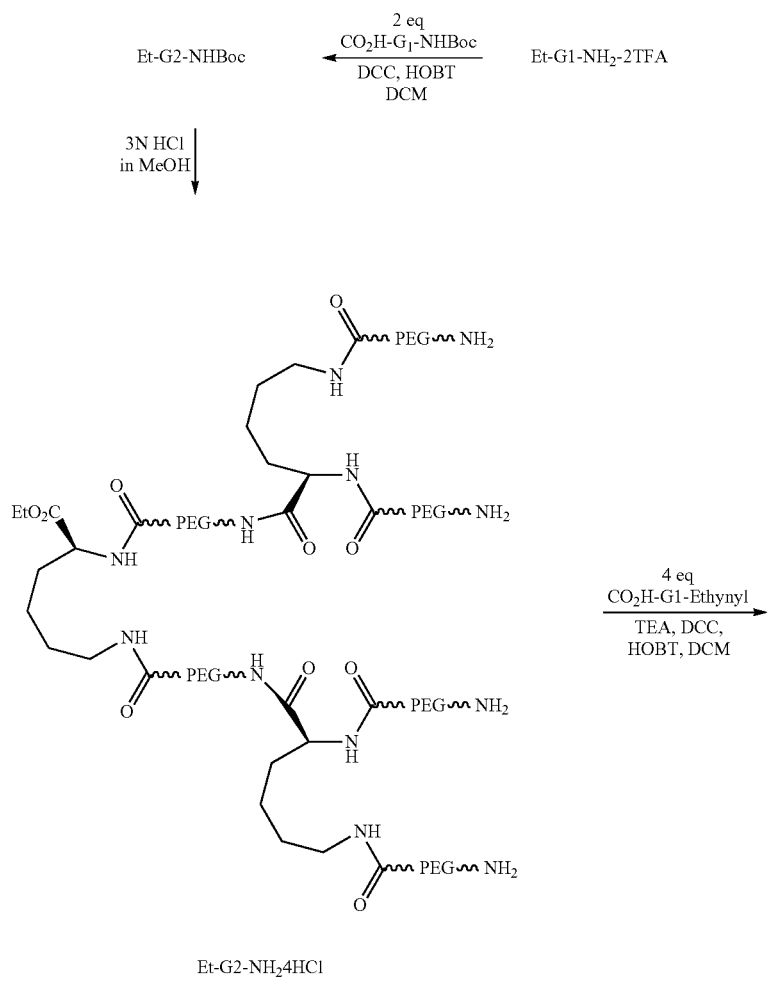

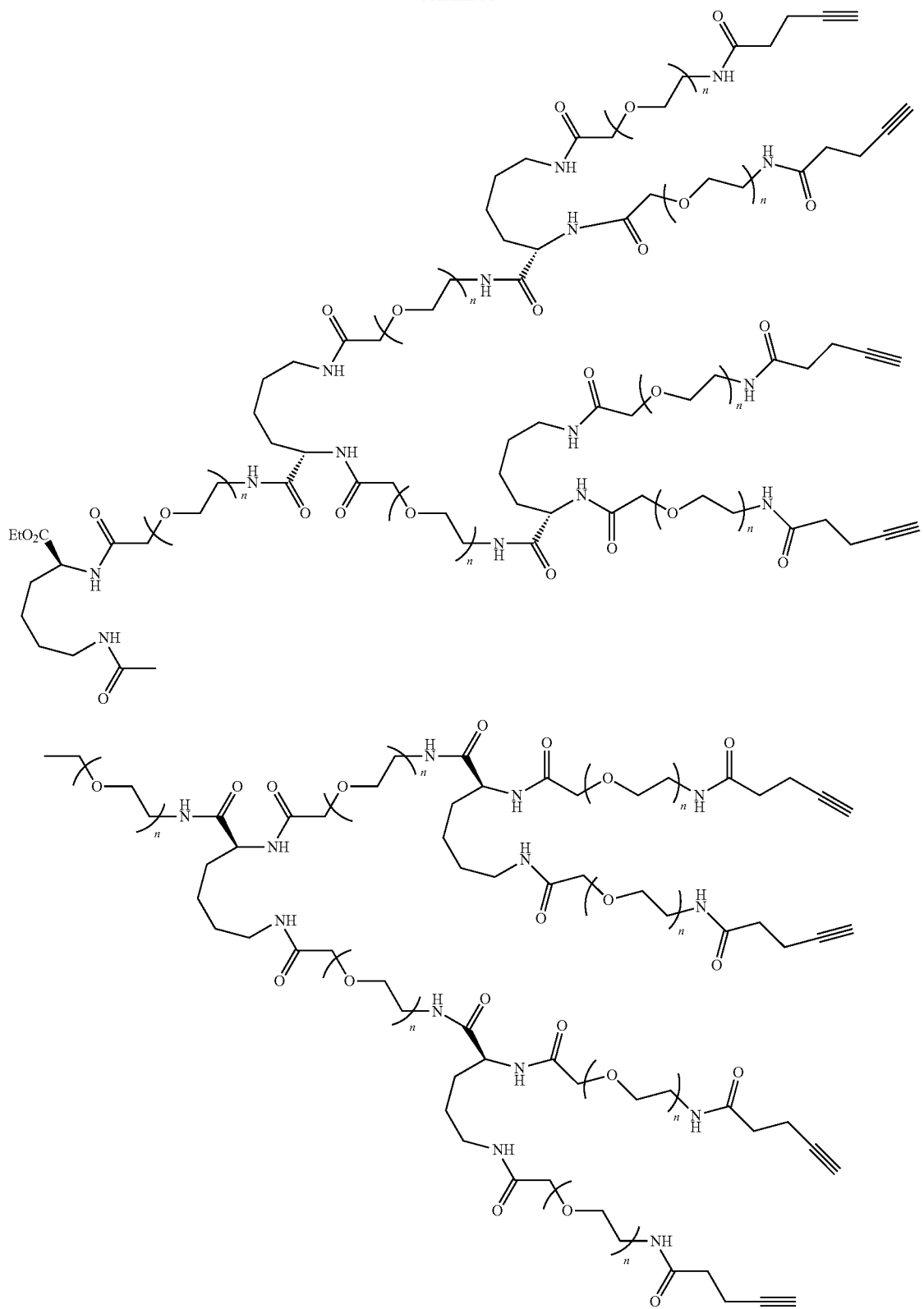
Et-G3-Ethynyl

Et-G2-NHBoc

HOBT (0.035 g, 0.227 mmol) was dried by azeotropic distillation using acetonitrile (20 mL). To the residue was added a solution of $CO_2H$-G1-NHBoc (0.890 g, 0.227 mmol) in dichloromethane (15 ml). DCC (0.047 g, 0.227 mmol) was added and the mixture was stirred for 3 hours. After addition of Et-G1-$NH_2$.2TFA (0.410 g, 0.103 mmol) and TEA (0.086 ml, 0.620 mmol), the reaction mixture was stirred overnight at room temperature. The mixture was filtered using a syringe filter and quenched with 0.1N HCl. All the organic volatiles were removed using a rotary evaporator. The resulting aqueous solution was passed through an Amberlite column and then an ion-exchange column using both DEAE Sepharose FF and SP Sepharose FF. The resulting aqueous solution was charged with NaCl (15% w/v) and extracted with dichloromethane. The combined organic phases were dried over anhydrous $Na_2SO_4$, filtered, concentrated using a rotary evaporator, and dried in vacuo to provide Et-G2-NHBoc (0.879 g, 74% yield). Ion-exchange analysis on both DEAE and SP column revealed all neutral species. $^1$H NMR (Varian, 500 MHz, 10 mg/mL $CDCl_3$) showed the usual backbone peak at 3.64 ppm (m, 4H, —$(OCH_2CH_2)_n$—) and other major peaks at 1.28 ppm (m, 3H, —$OCH_2CH_3$), 1.44 ppm (s, 36H, —NHBoc), 3.98-4.04 ppm (m, 12H two protons for each PEG, —NHC(=O)$CH_2$—$(OCH_2CH_2)_n$—), 4.19 ppm (m, 2H, —$OCH_2CH_3$), 4.59 ppm (q, 1H, —CH($CO_2$Et)NH—).

Et-G2-$NH_2$.4HCl

Et-G2-NHBoc (0.877 g, 0.076 mmol) was stirred with 20 mL of methanolic HCl (5 ml, 15.20 mmol) for 1 hour at room temperature. All the volatiles were removed under vacuum. The residue was dissolved in 30 mL of dichloromethane and washed with 25 mL of brine solution. The organic solution was dried over $Na_2SO_4$, filtered, concentrated, and dried in vacuo to give Et-G2-$NH_2$.HCl (0.883 g, quantitative yield). $^1$H NMR (Varian, 500 MHz, 10 mg/mL $CDCl_3$) showed the usual backbone peak at 3.64 ppm (m, 4H, —$(OCH_2CH_2)_n$—) and other major peaks at 1.28 ppm (m, 3H, —$OCH_2CH_3$), 3.94-4.04 ppm (m, 12H two protons for each PEG, —NHC(=O)$CH_2$—$(OCH_2CH_2)_n$—), 4.17 ppm (m, 2H, —$OCH_2CH_3$). The completion of deprotection was confirmed by disappearance of t-Boc proton peak at 1.44 ppm (s, 36H, —NHBoc).

Et-G3-Ethynyl

HOBT (0.051 g, 0.332 mmol) was dried by azeotropic distillation using 30 mL of acetonitrile. To the residue was added a solution of $CO_2H$-G1-Ethynyl (1.133 g, 0.292 mmol) in dichloromethane (33 ml). DCC (0.060 g, 0.292 mmol) was added and the mixture was stirred for 2 hours at room temperature to give a cloudy solution. After addition of Et-G2-NH2HCl (0.75 g, 0.066 mmol) and TEA (0.074 ml, 0.532 mmol), the mixture was stirred for 16 hours at room temperature. The mixture was quenched with 6 mL of 0.1 N HCl. All the organic volatiles were removed using a rotary evaporator and the remaining aqueous solution was diluted with 15 mL of water. The resulting aqueous solution was passed through an Amberlite column and then an ion-exchange column using both DEAE Sepharose FF and SP Sepharose FF to remove excess acid dendron species and amino species resulting from incomplete reaction. The resulting aqueous solution was charged with NaCl (15% w/v) and extracted with dichloromethane. The combined organic phases were dried over anhydrous $Na_2SO_4$, filtered, concentrated using a rotary evaporator, and dried in vacuo to provide pale yellow solids. Further purification was performed by stirring with 30 mL of diethyl ether for 30 minutes, filtering on a glass frit, and drying to give Et-G3-Ethynyl (1.221 g, 69% yield) as pale yellow crystalline material. Ion-exchange analysis on both DEAE and SP column revealed all neutral species. $^1$H NMR (Varian, 500 MHz, 10 mg/mL $CDCl_3$) showed the usual backbone peak at 3.64 ppm (m, 4H, —$(OCH_2CH_2)_n$—) and other major peaks at 1.28 ppm (m, 3H, —$OCH_2CH_3$), 2.03 (m, 2H, —$CH_2CH_2$CCH), 2.43 (t, 16H, —$CH_2CH_2$CCH), 2.53 (t, 16H, —$CH_2CH_2$CCH), 3.98-4.03 ppm (m, 28H two protons for each PEG, —NHC(=O)$CH_2$—$(OCH_2CH_2)_n$—), 4.17 ppm (m, 2H, —$OCH_2CH_3$), 4.40 ppm (q, 6H, —CH(CO—)NH—). 4.62 ppm (q, 1H, —CH($CO_2$Et)-NH—).

Example 13
PEG Et-G3-Ethynyl Dendrimer 26K attached to rotigotine 3-azidopropionate
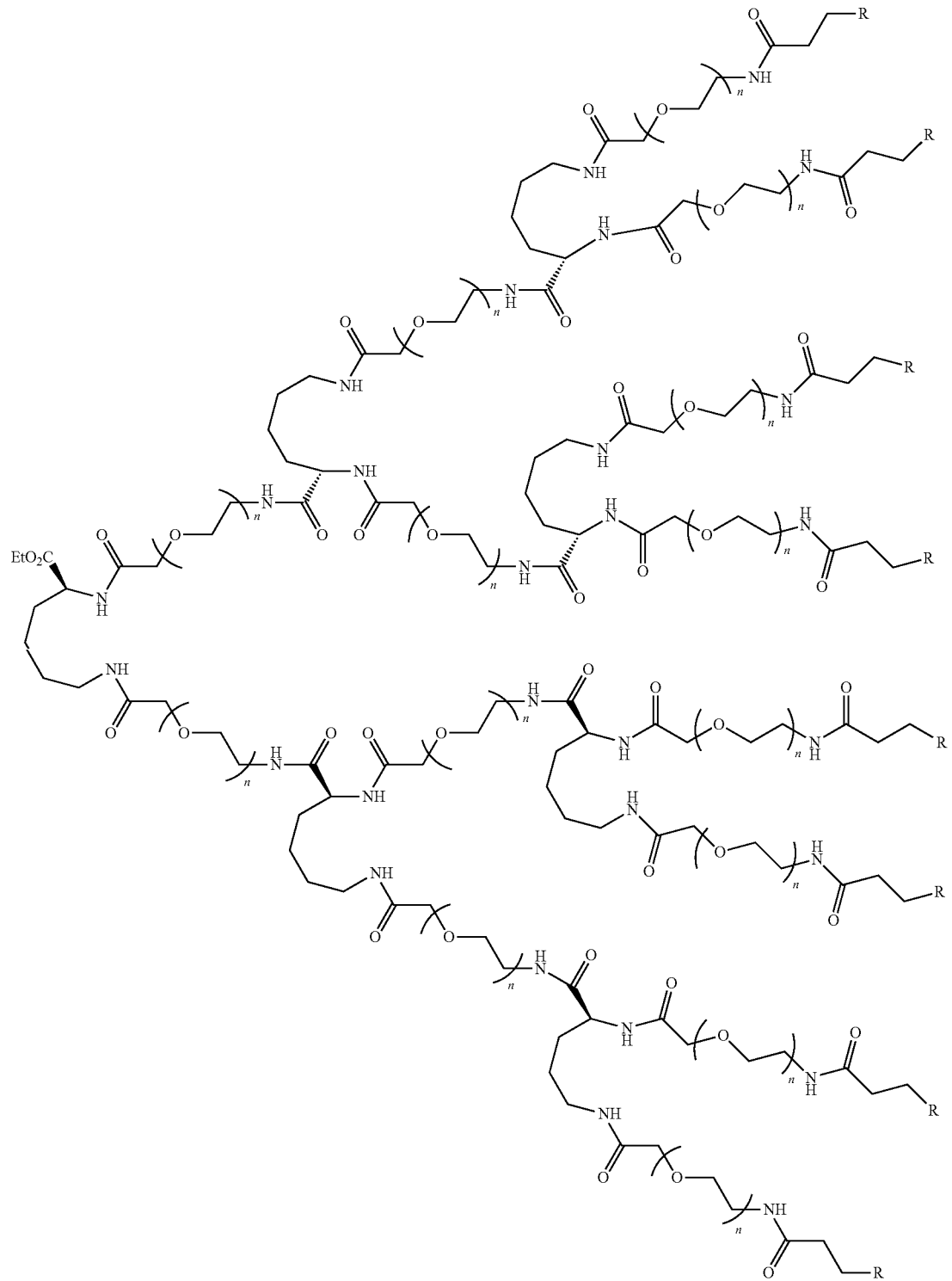
Et-G3-R

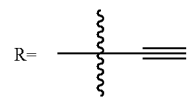

Et-G3-Ethynyl

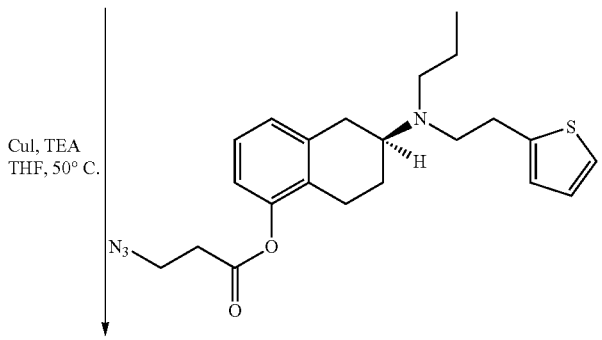

CuI, TEA
THF, 50° C.

Et-G3-Pr-Rotig

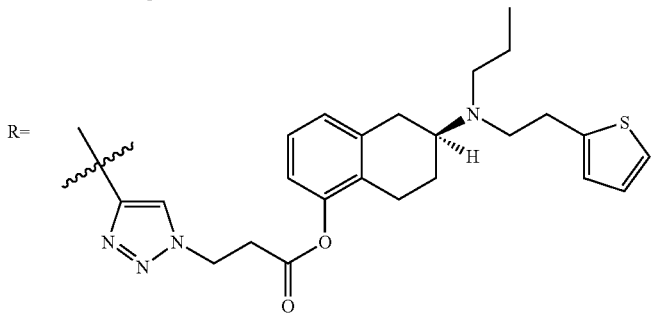

Rotigotine 3-azido propionate (0.192 g, 0.365 mmol) and Et-G3-Ethynyl (1.077 g, 0.041 mmol) were dissolved in THF (27.0 ml). Triethylamine (0.090 ml, 0.648 mmol) and CuI (0.123 g, 0.648 mmol) were added and the mixture was stirred for 40 hours at 50° C. After cooling to room temperature, the mixture was stirred with 12 mL of 0.1N HCl solution. After removing THF using a rotary evaporator, the resulting aqueous solution was diluted with 10 mL of water and passed through an Amberlite (IR-120H) column (50 mL) and a Dowex® M4195 column (50 mL) using 0.01% HCl solution as an eluent. The collected aqueous solution was stirred with 70 mL of dichloromethane using 22 g of NaCl (15 w/v % aqueous). Two layers were separated and the aqueous phase was stirred with 70 mL dichloromethane. The combined organic phases were dried over $Na_2SO_4$, filtered, concentrated, precipitated by adding into diethyl ether, filtered, and dried in vacuo. The resulting waxy solid was stirred with diethyl ether (20 mL) for 1 hour, filtered, and dried to give 0.997 g (82% yield) of the desired product, Et-G3-Rotig HCl, as pale yellow powder. The product had a rotigotine content of about 5% w/w. $^1$H NMR (Varian, 500 MHz, 10 mg/mL $CDCl_3$) showed the usual PEG peak at 3.64 ppm (m, 4H, —$(OCH_2CH_2)_n$—) and other major peaks at 1.28 ppm (m, 3H, —$OCH_2CH_3$), 3.97-4.03 ppm (m, 28H two protons for each PEG, —NHC(=O)$CH_2$—$(OCH_2CH_2)_n$—), 4.17 ppm (m, 2H, —$OCH_2CH_3$), 4.41 ppm (q, 6H, —CH(CO)NH—), and 4.62 ppm (q, 1H, —CH($CO_2$Et)NH—). Rotigotine peaks were revealed at 1.04 ppm (t, 3H, —$CH_2CH_2CH_3$), 4.73 ppm (m, 2H, triazole-$CH_2CH_2$C(=O)O-Rotigotine), 6.89-7.20 ppm (m, 6H, aromatic and thiophenyl H), 7.70 (br s, 1H, triazole H). The number of rotigotine molecules on the dendrimer was determined as 5.6 by both $^1$H NMR and reverse phase HPLC analysis. 'Click' reaction was monitored by the disappearance of the terminal peaks at 2.03 (m, 2H, —$CH_2CH_2$CCH) and 2.43 (t, 16H, —$CH_2CH_2$CCH), and by the appearance of a triazole proton peak at 7.70 ppm.

Example 14

Preparation of 4-Arm PEG rotigotine glycine ester (10K)

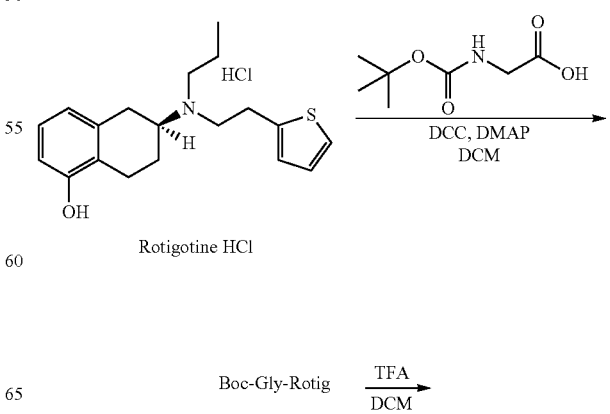

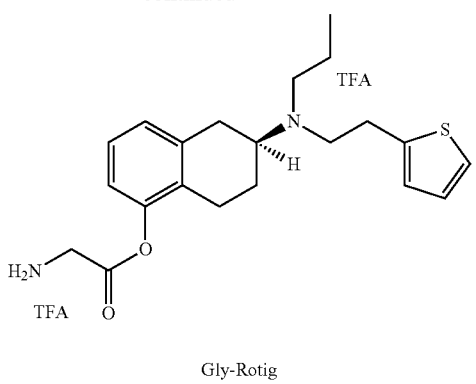

Gly-Rotig

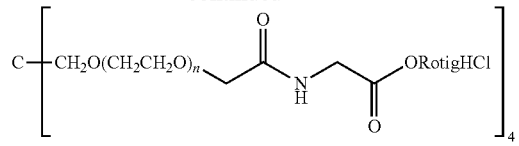

Glycine-Rotigotine synthesis:

Rotigotine HCl (1.2 g, 3.41 mmol) and Boc-Glycine-OH (1.195 g, 6.82 mmol) were dissolved in dichloromethane (150 ml) to give a suspension. After addition of DMAP (0.625 g, 5.11 mmol) and DCC (1.407 g, 6.82 mmol), the mixture was stirred for 16 hours at room temperature. The mixture was filtered using filter paper and the filtrate was quenched with 51 mL of 0.1 N HCl (5.11 mmol). The layers were separated and the aqueous phase was extracted with 7 mL of dichloromethane. The combined organic phases were washed with water and then with brine, dried over $Na_2SO_4$, filtered, concentrated using a rotary evaporator, and dried in vacuo to give a crude pale yellow solid. The crude material was stirred with diethyl ether (50 mL) for 30 minutes, filtered on a glass frit, washed with diethyl ether, and dried in vacuo to give a pale yellow powder Boc-Gly-Rotigotine.HCl (1.258 g, 75% yield).

$^1$H NMR (Varian, 500 MHz, 10 mg/mL $CDCl_3$) showed peaks at 1.04 ppm (t, 3H, —$CH_2CH_2CH_3$), 1.47 ppm (s, 9H, —NHBoc), 1.96 ppm (m, 2H), 2.06 ppm (m, 1H), 2.60 ppm (m, 2H), 2.93 ppm (m, 1H), 3.04 ppm (m, 1H), 3.13 ppm (m, 1H), 3.26 ppm (m, 2H), 3.40 ppm (m, 2H), 3.52 ppm (m, 1H), 3.66 ppm (m, 2H), 4.17 ppm (d, 2H, —NHCH$_2$C(=O)—), 5.08 ppm (s, 1H, —C(=O)NHCH$_2$—), 6.95 ppm (m, 3H, aromatic), 7.06 ppm (t, 1H, thiophenyl), and 7.20 ppm (m, 2H, thiophenyl).

The Boc-Gly-Rotigotine HCl was deprotected by first dissolving the product (1.258 g, 2.55 mmol) in dichloromethane (64 ml). After addition of trifluoroacetic acid (9.83 ml, 128 mmol), the reaction mixture was stirred for 1 hour at room temperature and then all the volatiles were removed using a rotary evaporator. The residue (dark yellow) was dissolved in methanol and precipitated by adding into diethyl ether (40 mL). The pale yellow precipitate was filtered using a glass frit and dried to give Gly-Rotigotine.2TFA (1.140 g, 79% yield).

$^1$H NMR (Varian, 500 MHz, 10 mg/mL $CDCl_3$) showed peaks at 0.98 ppm (d, 3H, —$CH_2CH_2CH_3$), 1.72 ppm (m, 1H), 1.83 ppm (m, 2H), 2.33 ppm (m, 1H), 2.51 ppm (m, 2H), 2.80 ppm (m, 1H), 3.00 ppm (m, 2H), 3.12 ppm (m, 2H), 3.30 ppm (m, 3H), 3.73 ppm (m, 1H), 4.03 ppm (q, 2H, $NH_2CH_2C$(=O)O—), 6.80 ppm (d, 1H, aromatic), 6.92 ppm (m, 2H, aromatic), 6.99 ppm (d, 1H, thiophenyl), 7.08 ppm (t, 1H, thiophenyl), and 7.17 ppm (d, 1H, thiophenyl).

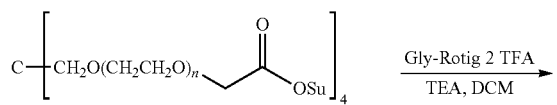

4-Arm PEG-SCM 10K (2.02 g, 0.165 mmol) and Gly-Rotigotine.2TFA (0.373 g, 0.658 mmol) were dissolved in dichloromethane (16.5 ml). TEA (0.229 ml, 1.645 mmol) was added to give a yellow clear solution. After stirring for 16 hours at room temperature, the mixture was quenched with 16 mL of 0.1N HCl solution and charged with 1.6 g of NaCl (10 w/v % for water). Two layers were separated and the aqueous phase was extracted with 16 mL of dichloromethane. The combined organic phases were dried over $Na_2SO_4$, filtered, and concentrated. The crude extract was dissolved in 40 mL of water and passed through an Amberlite (IR120H) column to remove small molecules. The collected aqueous solution was stirred with 50 mL of dichloromethane and charged with 10.5 g of NaCl (15 w/v % of water). Two layers were separated and the aqueous phase was extracted with an additional 50 mL of dichloromethane. The combined organic phases were dried over $Na_2SO_4$, filtered, concentrated, and dried in vacuo to give the desired product 4-arm PEG-Gly-Rotigotine.HCl 10K (1.89 g, 85% yield). The product had a rotigotine content of about 6% w/w.

$^1$H NMR (Varian, 500 MHz, 10 mg/mL $CDCl_3$) showed the polymer backbone peaks at 3.64 ppm (m, 4H, —($OCH_2CH_2$)$_n$—) and other major peaks at 1.04 ppm (d, 3H, —$CH_2CH_2CH_3$), 6.96 ppm (m, 3H, aromatic), 7.05 ppm (t, 1H, thiophenyl), 7.20 ppm (m, 2H, thiophenyl), and 7.80 ppm (m, 1H, triazole). The average number of rotigotine molecules on each polymer was determined to be 3.1 by $^1$H NMR analysis.

Example 15

Preparation of 4-Arm PEG rotigotine glycine ester (20K)

The glycine-rotigotine.2TFA salt was prepared as described in example 14. The 4-arm PEG-SCM 20K (2.007 g, 0.098 mmol) and Gly-Rotigotine.2TFA (0.222 g, 0.393 mmol) were dissolved in dichloromethane (9.8 ml). TEA (0.137 ml, 0.981 mmol) was added to give a yellow clear solution. After stirring for 16 hours at room temperature, the mixture was quenched with 9.8 mL of 0.1N HCl solution and charged with 1.0 g of NaCl (10 w/v % for water). The layers were separated and the aqueous phase was extracted with 10 mL of dichloromethane. The combined organic phases were dried over $Na_2SO_4$, filtered, and concentrated. The crude extract was dissolved in 40 mL of water and passed through Amberlite (IR120H) column to remove all the small molecules. The collected aqueous solution was stirred with 50 mL of dichloromethane and charged with 10.5 g of NaCl (15 w/v % of water). The layers were separated and the aqueous phase was extracted with 40 mL of dichloromethane. The combined organic phases were dried over $Na_2SO_4$, filtered, concentrated, and dried in vacuo to give the desired product 4-arm PEG-Gly-Rotigotine.HCl 20K (1.58 g, 74% yield). The product had a rotigotine content of about 3% w/w.

$^1$H NMR (Varian, 500 MHz, 10 mg/mL $CDCl_3$) showed the polymer backbone peaks at 3.64 ppm (m, 4H, —($OCH_2CH_2$)$_n$—) and other major peaks at 1.03 ppm (d, 3H, —$CH_2CH_2CH_3$), 6.95 ppm (m, 3H, aromatic), 7.06 ppm (t, 1H, thiophenyl), 7.20 ppm (m, 2H, thiophenyl), and 7.81 ppm (m, 1H, triazole). The average number of rotigotine molecules on each polymer was determined to be 2.53 by $^1$H NMR analysis.

Example 16

Synthesis of Oxidized Dextran (20K)

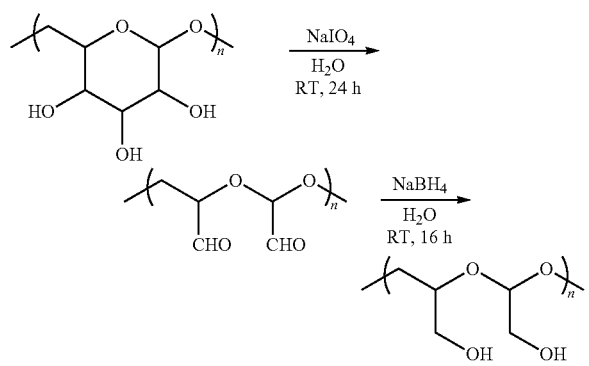

Polyal (Oxidized Dextran) Synthesis:

(See M. I. Papisov, U.S. Pat. No. 5,811,510). Sodium periodate (5.58 g, 26 mmol) was dissolved in 30 mL of DI-H$_2$O in a 100 mL one-neck round-bottom flask. The flask was covered with aluminum foil. In a 20 mL vial, 2.0 g of dextran (0.13 mmol, M$_n$: 15,340 g/mole, M$_p$: 22,630 g/mole, PD: 2.11) was dissolved in 15 mL of DI-H$_2$O and this solution was slowly added to the round-bottom flask. The vial was rinsed with 15 mL of DI-H$_2$O and the rinse solution was also added into the round-bottomed flask. The clear colorless solution was stirred at room temperature for 24 h. At the end of this time, the aqueous solution was transferred into two Slide-A-Lyzer 2K dialysis cassettes and dialysis was conducted in water overnight. This aqueous solution (~60 mL) was used in the next step.

Polyalcohol Synthesis from Polyal:

1.134 g of sodium borohydride (30 mmol) was dissolved in 10 mL of DI-H$_2$O in a 100 mL one-neck round-bottomed flask. The aqueous solution from the previous step was then added slowly into the round-bottom flask. The solution was stirred for 18 h. The pH of the solution was adjusted to 6 using 3M HCl and the solution was again dialyzed using three 10K MWCO dialysis cassettes for two days. The aqueous solution was concentrated to 5 mL and then lyophilized for two days to give 1.56 g of the polyalcohol in 94% yield.

$^1$H NMR (DMSO-d6, δ, ppm, TMS): 3.35 (2H, —OCH$_2$CH(CH$_2$OH)O—), 3.48 (2H, —OCH(CH$_2$OH)O—), 3.58-3.70 (2H, —OCH$_2$CH(CH$_2$OH)O—), 3.64 (1H, —OCH$_2$CH(CH$_2$OH)O—), 4.62 (2H, —OCH$_2$CH(CH$_2$OH)OCH(CH$_2$OH)O—), 4.70 (1H, —OCH(CH$_2$OH)O—).

$^{13}$C NMR (DMSO-d6, δ, ppm, TMS): 64.56 (—OCH$_2$CH(CH$_2$OH)O—), 65.10 (—OCH(CH$_2$OH)O—), 68.96 (—OCH$_2$CH(CH$_2$OH)O—), 79.88 (—OCH$_2$CH(CH$_2$OH)O—), 105.86 (—OCH(CH$_2$OH)O—).

GFC: M$_n$: 11,100 g/mole, M$_p$: 19,270 g/mole, PD: 2.41

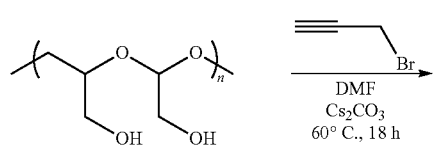

-continued

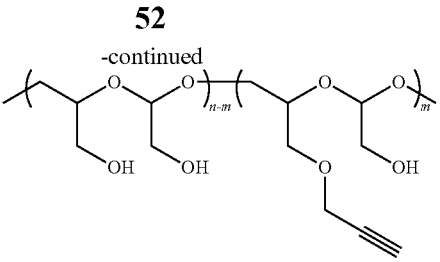

Polyalcohol Propargyl Bromide Reaction:

Polyalcohol (840.0 mg, 5×10$^{-5}$ mole, M$_n$: 11,100 g/mole, M$_p$: 19,270, PD: 2.4) was dissolved in 10 mL of dimethylformamide in a 25 mL round-bottom flask. Toluene (5 mL) was then added into the round-bottom flask. Toluene was evaporated at 50° C. and 40 mbar using a rotary evaporator. 407.5 mg of cesium carbonate (1.25×10$^{-3}$ mole) was then added into the round-bottom flask. The mixture was stirred for 3 h under argon at 60° C. 234.0 mg of propargyl bromide solution (80% solution in toluene, 187.5 mg of propargyl bromide, 1.25×10$^{-3}$ mole) was added into the round-bottom flask. The cloudy solution was stirred at 60° C. for 34 h under argon. At the end of this time, the yellow cloudy solution was cooled to room temperature, filtered through a 30 mL frit, and the filtrate was concentrated to dryness. The polymer was dissolved in 15 mL of DI-H$_2$O and washed with dichloromethane twice (2×45 mL). The dichloromethane phase was washed with 15 mL of DI-H$_2$O. Aqueous phases were separated, combined and evaporated to remove any residual dichloromethane. The aqueous solution was then dialyzed using a 2K MWCO dialysis cassette overnight. The water was removed and the polymer was dried under high vacuum to give 730.0 mg of the final product.

$^1$H NMR (DMSO-d6, δ, ppm, TMS): 3.35 (2H, —OCH$_2$CH(CH$_2$OH)O—), 3.48 (2H, —OCH(CH$_2$OH)O—), 3.58-3.70 (2H, —OCH$_2$CH(CH$_2$OH)O—), 3.64 (1H, —OCH$_2$CH(CH$_2$OH)O—), 4.18 (4H, —OCH$_2$CH(CH$_2$OCH$_2$C≡CH)OCH(CH$_2$OCH$_2$C≡CH)O—), 4.62 (2H, —OCH$_2$CH(CH$_2$OH)OCH(CH$_2$OH)O—), 4.70 (1H, —OCH(CH$_2$OH)O—). From NMR data, the average value of 'n' is 78 and of 'm' is 5

Example 17

Oxidized Dextran (20K) attachment to 3-azidopropyl rotigotine

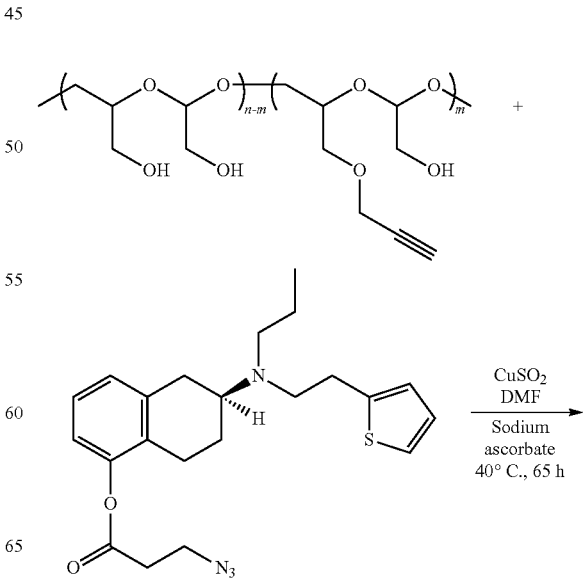

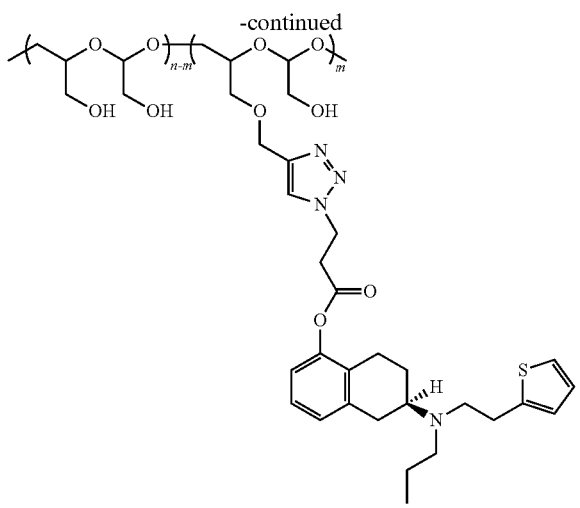

Three hundred and forty two milligrams (342.0 mg) of 3-azidopropionyl rotigotine.TFA ($6.5\times10^{-4}$ mole) was weighed in a 100 mL round-bottom flask and 835.0 mg of oxidized dextran with acetylene pendents ($6.5\times10^{-5}$ mole; average 'n' value of 89, 'm' value of 6) and was added into the flask. Eighty milliliters (80 mL) of dimethylformamide was then added into the flask to completely dissolve the polymer. 64.5 mg of copper sulfate ($2.6\times10^{-4}$ mole) and 103.0 mg of sodium ascorbate ($5.2\times10^{-4}$ mole) were then added to the round-bottom flask. The round-bottom flask was closed with a rubber septum and the solution was stirred at 40° C. under argon overnight. More copper sulfate (258.0 mg, $1.04\times10^{-3}$ mole) and sodium ascorbate (412.0 mg, $2.08\times10^{-3}$ mole) were added and the solution was stirred overnight at 40° C. More copper sulfate (322.5 mg, $1.3\times10^{-3}$ mole) and sodium ascorbate (515.0 mg, $2.6\times10^{-3}$ mole) were added and the solution was stirred overnight at 40° C. At the end of this time, the solution was cooled to room temperature, filtered through a coarse frit, and the solvent removed by rotary evaporation. The residue was dissolved in 60 mL of DMF, filtered, concentrated to 10 mL and precipitated into diethyl ether (200 mL). The solvents were decanted and the polymer was dried under vacuum overnight to give 362.0 mg of the final product. The product had a rotigotine content of about 5% w/w.

$^1$H NMR (DMSO-d6, δ, ppm, TMS): 0.86 (3H, —NCH$_2$CH$_2$CH$_3$); 1.4-3.6 (total of 17H, aliphatic CH and CH$_2$ peaks of rotigotine); 3.36 (2H, —OCH$_2$CH(CH$_2$OH) O—), 3.47 (2H, —OCH$_2$(CH$_2$OH)O—), 3.57-3.70 (2H, —OCH$_2$CH(CH$_2$OH)O—), 3.64 (1H, —OCH$_2$CH(CH$_2$OH) O, 4.62 (2H, —OCH$_2$CH(CH$_2$OH)OCH(CH$_2$OH)O—), 4.70 (1H, —OCH(CH$_2$OH)O—); 6.80-7.29 (6H, —CH peaks of 1,2,3,4-tetrahydronaphtalene and —CH peaks of 2-thiophene); 8.14 (1H, —CH peak of triazole).

Example 18

Hydrolysis of Rotigotine from Polymer Conjugates

The hydrolysis of rotigotine from the three types of linkers on the poly(oxazoline)-rotigotine conjugates was examined in rat plasma. Four milliliters of rat plasma was placed in a test tube, and then spiked with approximately 16 mg of each poly(oxazoline) drug conjugate dissolved in 400 μL of 5% dextrose solution. The test tubes were placed in a 37° C. water bath and allowed to incubate for approximately 48 hours. At regular time intervals, a 100 μL aliquot of plasma was taken and placed in a 1.5 mL centrifuge tube, neutralized with 5 μL of dilute acid solution (3M HCl or 30% TFA), and treated with ~500 μL of acetonitrile to precipitate the plasma proteins and dissolve the rotigotine. The tube was centrifuged at 14,000 rpm for 5 minutes. The supernatant was removed, filtered, placed in an HPLC vial, and assayed by reverse phase chromatography using a Zorbax C8 300SB, 5μ, 4.6×150 mm column fixed to an Agilent 1100 chromatogarphy system fitted with a variable UV detector set at 228 nm. The mobile phase was 0.1% TFA in water (A) and 0.1% TFA in acetonitrile (B) eluting a rate of 1 mL/min. A standard curve was created by spiking a known concentration of drug in plasma and extracting and assaying the free drug as described above. The amount of drug in each aliquot was calculated from the standard curve above and a plot of the concentration of drug released versus time was generated. The half-life of each poly(oxazoline)-rotigotine conjugate was calculated and shown in Table 1. Table 1 shows that changes in the linking group, as well as the nature of the polymer (POZ vs. PEG vs. modified dextran), affect the hydrolytic release of rotigotine from the polymer conjugate. As can be seen in Table 1, Only POZ polymers provided extended half-life of the agent. PEG and dextran polymers were not effective. As a result, POZ polymers can be "tuned" to release the agent with a desired release profile without an initial burst effect. Of particular note, polymers that release rotigotine fast (under 15 minutes) would not be expected to work for the treatment of dopamine deficiency disorders by a daily or weekly subcutaneous injection.

TABLE 1

Effect of linker and polymer on rate of hydrolysis release of rotigotine from rotigotine esters (polymer-triazine-alkyl-CO-O-Rotigotine) in plasma, pH 7.4, 37° C.

| Polymer* | Alkyl Linker | Half-Life |
| --- | --- | --- |
| POZ* | —CH$_2$— | 2.4 ± 0.28 hours (2 batches) |
| POZ* | —CH$_2$(CH$_3$)— | 7.1 hours |
| POZ* | —CH$_2$CH$_2$— | 11.9 ± 4.2 hours (6 batches) |
| POZ* | —CH$_2$CH$_2$CH$_2$— | 5.0 hours |
| PEG 4-arm$^\$$ | —CH$_2$CH$_2$— | 8 minutes |
| PEG Dendrimer$^@$ | —CH$_2$CH$_2$— | 11 minutes |
| PEG 4-arm$^!$ | See specification | <5 minutes |
| Modified Dextran$^\#$ | —CH$_2$CH$_2$— | <2 minutes |

*POZ is MW 20,000, acid terminus, 10 triazine pendents.
$^\$$PEG see examples 10 and 11 for structure
$^@$see examples 12 and 13 for structure
$^!$see examples 14 and 15 for structure
$^\#$see examples 16 and 17 for structure Example 19

Pharmacokinetics of rotigotine in rat after intravenous and subcutaneous administration of H-[(Acetyl-Rotigotine)$_{10}$(EOZ)$_{190}$]-COOH 20K and H-[(Propionyl-Rotigotine)$_{10}$(EOZ)$_{190}$]-COOH 20K To study the pharmacokinetics of the POZ conjugates described herein, in vivo studies were conducted with male Sprague-Dawley rats. Twenty-seven male cannulated Sprague-Dawley rats (300-350 g) were divided into nine groups of 3 animals per group. Groups I-II received a single subcutaneous (SC) dose (right flank) of POZ acetyl rotigotine (as described in Example 6) at equivalent doses of 1.6 and 6.4 mg/kg. Groups III-IV received a single subcutaneous (SC) dose (right flank) of POZ propyl rotigotine (as described in Example 7) at equivalent doses of 1.6 and 6.4 mg/kg. Group V received a single subcutaneous (SC) dose (right flank) of rotigotine hydrochloride at an equivalent dose of 0.5 mg/kg. Groups VI-VII received a single intravenous (IV) dose (lateral tail vein) of POZ acetyl rotigotine (as described in Example 6) at equivalent doses of 0.5 and 2.0 mg/kg. Groups VIII-IX received a single intravenous (IV) dose (lateral tail vein) of POZ propyl rotigotine (as described in Example 7) at equivalent doses of 0.5 and 2.0 mg/kg. The test articles were dissolved in 5% dextrose injection and filtered prior to each injection. Serial blood samples were obtained from each intravenously dosed animal through the cannulated catheter, at time intervals of end of injection, 12, 24, 48, 96 and 168 hours. The time intervals for the subcutaneously dosed animals were 6, 12, 24, 48, 96 and 168 hours. The blood was processed to collect the plasma which was stored at −70° C. before analysis. The plasma samples were extracted with acetonitrile using d3-rotigotine as an internal standard and the analytes in the extract were assayed by chromatographic analysis on LC/MS-MS system using a C-18 reverse phase column with 0.9 um silica coreshell (Accucore™, Thermo Scientific, 30×2.1 mm ID and 2.6 micron particle size). The mobile phase was ammonium formate 10 mM pH3.0 (solvent A); and 90% acetonitrile, 10% methanol, and 0.1% formic acid (solvent B), eluting at 0.6 mL/min.

The plasma concentration of rotigotine (ng/mL) after intravenous and subcutaneous injection is shown in FIGS. 2 and 3, respectively. These results show that POZ conjugates of rotigotine, whether dosed intravenously or subcutaneously, will reduce the clearance rate of rotigotine from the blood when compared to the parent molecule alone. The terminal plasma half-life (t½) for rotigotine, POZ acetyl rotigotine and POZ propyl rotigotine was 2.8, 16 and 60 h, respectively. However, there is a striking difference in the PK profiles of the POZ-conjugates POZ acetyl rotigotine and POZ propyl rotigotine when compared IV vs SC. POZ-conjugates delivered IV are generally cleared in a bi-phasic pattern with little difference between POZ acetyl rotigotine and POZ propyl rotigotine. However, when the two are compared following SC administration there is a marked difference. POZ acetyl rotigotine has essentially the same PK profile when delivered either SC or IV. POZ propyl rotigotine has a markedly prolonged PK profile that is near "zero order" kinetics. The size and length of the linker plays a role in the release of the agent, in this case rotigotine. The levels of rotigotine released from the polymer conjugate and measured in rat plasma from day 1 to day 7 are higher for the propyl linker than the acetyl linker. The initial plasma concentration of rotigotine during the first 12 hours is lower for POZ propyl rotigotine when compared to the POZ acetyl rotigotine compound. At 12 hours, the $C_{max}$ values of plasma rotigotine were 6 ng/mL for POZ propyl rotigotine versus for 48 ng/mL for the POZ acetyl rotigotine when dosed SC at the dose of 1.6 mg/kg. This shows that controlled delivery of an agent can be "tuned" to release the agent with a desired release profile without an initial burst effect based on the nature of the hydrolyzable linker, the size of the POZ polymer, the route of administration (e.g. subcutaneous) or a combination of the foregoing.

Example 20

Pharmacokinetics of rotigotine in monkey after subcutaneous administration of H-[(α-Methyl-Acetyl-Rotigotine)$_{10}$(EOZ)$_{190}$]-COOH 20K and H-[(Propionyl-Rotigotine)$_{10}$(EOZ)$_{190}$]-COOH 20K The pharmacokinetics of the POZ conjugates of rotigotine was measured in normal, treatment-naïve female macaques. Animals were randomly assigned into four treatment groups, each N=3. Animals received one subcutaneous dose of either POZ alpha methyl acetyl rotigotine (as described in Example 8) or POZ propyl rotigotine (as described in Example 7) at doses of either 1.5 mg/kg or 4.5 mg/kg (based on rotigotine equivalents). The test articles were dissolved in 5% dextrose injection and filtered prior to each injection. Serial venous blood samples were obtained from each animal prior to administration of experimental agents on Day 1 and subsequently at 15 min, 30 min, 1 h, 2 h, 4 h, 6 h, 8 h, 24 h, 48 h, 96 h, 192 h, 240 h and 336 h. The blood was processed to collect the plasma which was stored at −70° C. before analysis. These plasma samples were processed and assayed by chromatographic analysis on LC/MS-MS system as described in Example 11.

Figure 4:
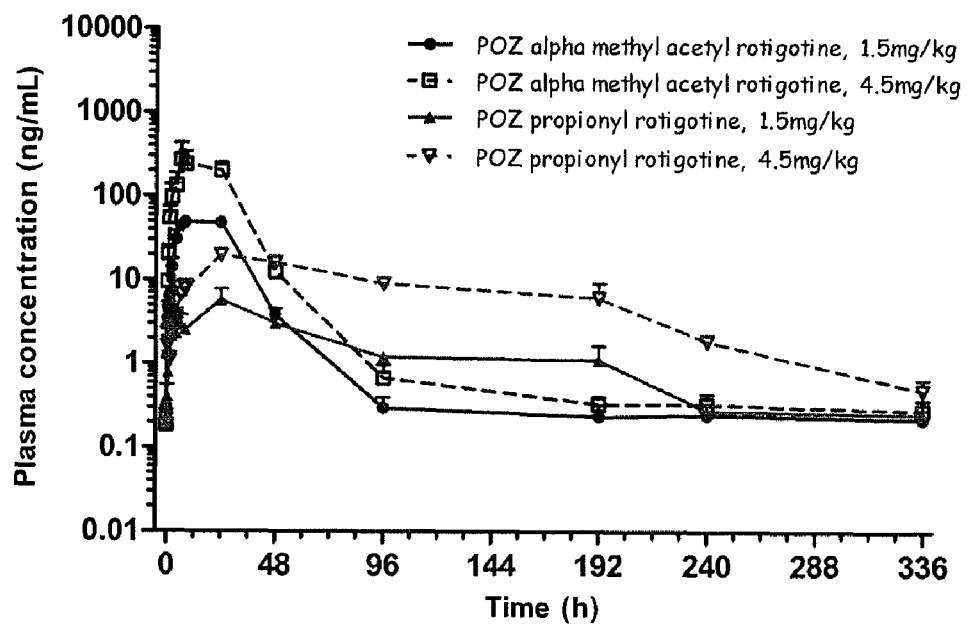
FIG. 4 shows the pharmacokinetic profile of rotigotine after subcutaneous dosing of POZ-rotigotine in female Cynomolgus monkeys.

The plasma concentration of rotigotine (ng/mL) after subcutaneous injection is shown in FIG. 4. These results show that POZ conjugates of rotigotine reduce the clearance rate of rotigotine from the blood. The average terminal plasma half-life (t½) of rotigotine from POZ alpha methyl acetyl rotigotine and POZ propionyl rotigotine was 9 and 60 h, respectively. Once again, the POZ propyl rotigotine has a markedly prolonged PK profile that is near "zero order" kinetics. The initial plasma concentrations of rotigotine during the first 12 hours are lower for POZ propyl rotigotine when compared to the POZ alpha methyl acetyl rotigotine compound. From 4 to 192 hours, the average $C_{ss}$ value of plasma rotigotine was between 1 and 6 ng/mL for POZ propyl rotigotine at the 1.5 mg/kg dose.

Example 21

Efficacy of H-[(Acetyl-Rotigotine)$_{10}$(EOZ)$_{190}$]-COOH 20K and H-[(Propionyl-Rotigotine)$_{10}$(EOZ)$_{190}$]-COOH 20K in the 6-OHDA rat model following subcutaneous administration To study the efficacy of the POZ conjugates described herein, in vivo studies were conducted with female Sprague-Dawley rats. Female Sprague-Dawley rats (275-350 g) were used in the study. Each animal underwent stereotaxic surgery and received a unilateral lesion of the right nigrostriatal pathway via injection of 12.5 μg of 6-hydroxydopamine (6-OHDA) into a single site in the medial forebrain bundle. Rats were monitored over two weeks and underwent behavioral assessment (on day −7) via the cylinder test. Animals lacking overt behavioral asymmetry (>85% ipsilateral forelimb use) were excluded from the study. The rats were them randomly assigned to one of six treatment groups (each N=8). The groups were as follows: vehicle control (Group A); rotigotine hydrochloride 0.5 mg/kg (Group B); rotigotine hydrochloride 3 mg/kg (Group C); H-[(Acetyl-Rotigotine)$_{10}$(EOZ)$_{190}$]-COOH 20K (as described in Example 6) 1.6 mg/kg (Group D); H-[(Propionyl-Rotigotine)$_{10}$(EOZ)$_{190}$]-COOH 20K (as described in Example 7) 1.6 mg/kg (Group E); and H-[(Propionyl-Rotigotine)$_{10}$(EOZ)$_{190}$]-COOH 20K (as described in Example 7) 6.4 mg/kg (Group F). The rats received a single subcutaneous dose (2 mL/kg) of vehicle (5% dextrose) or test compound dissolved in 5% dextrose.

Each group of animals (A-F) were independently assessed rat for rotational behavior and forelimb symmetry on day 1, day 2, day 5 and day 9. In the rotational test, the animals were placed in an automated rotometer apparatus (MedAssociates, USA) and the net number of rotations contraversive to the lesion were recorded over a period of 6 hours on each day. In the forelimb symmetry test, the rats are placed in a clear glass cylinder without top (15 cm diameter×45 cm tall). The number of times each paw touches the side of the cylinder during an individual rear is recorded over a 10 minute observation on each day. The first limb in any rear to touch the wall is scored a single point. If both limbs contact within 0.4 s of each other, then this is scored as a 'both'. All subsequent exploratory movements about the wall using that limb are scored independently until the other limb contacts the wall with weight support. Alternating stepping motions involving both paws one after the other receive a single score for both. The net number of contralateral touches are calculated and considered a favorable response.

Table 2 summarizes the results of the rotational test:

TABLE 2

| Compound | Dose (mg/kg) | Net number of contraversive turns/6 h period (Average ± SEM; n = 8) | |
|---|---|---|---|
| | | Day 1 | Day 5 |
| Vehicle | 0 | −56 ± 20 | −25 ± 11 |
| Rotigotine | 0.5 | 983 ± 405 | −49 ± 9 |
| Rotigotine | 3.0 | 1570 ± 312* | −39 ± 15 |
| POZ Acetyl Rotigotine 20K | 1.6 | 872 ± 232 | −14 ± 14 |
| POZ Propionyl Rotigotine 20K | 1.6 | 1408 ± 286* | 68 ± 60 |
| POZ Propionyl Rotigotine 20K | 6.4 | 1272 ± 405* | 5142 ± 777** |

*/**represents P < 0.01 or P < 0.001 cf. vehicle (1-way ANOVA with Dunnett's post-hoc test).

All treatments show positive rotational behaviors (contraversive turns) on day 1 of dosing. Only POZ propyl rotigotine shows activity on day 5, with marked and continuous contraversive rotations at the high dose of 6.4 mg/kg. This favorable response is due to the high and sustained rotigotine drug levels in blood on day 5, which was observed in the preceding pharmacokinetic study.

Table 3 summarizes the results of the forelimb asymmetry test:

TABLE 3

| Compound | Dose (mg/kg) | Net ipsiversive forelimb use as a percentage of total forelimb use (Average ± SEM; n = 8) | |
|---|---|---|---|
| | | Day 2 | Day 5 |
| Vehicle | 0 | 88 ± 7% | 85 ± 6% |
| Rotigotine | 0.5 | 60 ± 13% | 94 ± 6% |
| Rotigotine | 3.0 | 9 ± 13%* | 85 ± 8% |
| POZ alpha methyl acetyl Rotigotine 20K | 1.6 | 50 ± 13% | 85 ± 10% |
| POZ Propyl Rotigotine 20K | 1.6 | 0 ± 14%** | 31 ± 13%* |
| POZ Propyl Rotigotine 20K | 6.4 | −2 ± 26%** | −6 ± 16%** |

*/**represents P < 0.01 or P < 0.001 cf. vehicle (1-way ANOVA with Dunnett's post-hoc test).

All treatments show positive ipsiversive forelimb use on day 1 of dosing. Only POZ propyl rotigotine shows activity on day 5, with marked and continuous ipsiversive forelimb use at the both doses of 1.6 and 6.4 mg/kg. This favorable response is due to the high and sustained rotigotine drug levels in blood on day 5, which was observed in the pharmacokinetic study.

What is claimed is:

1. A polymer conjugate of the general formula (I),

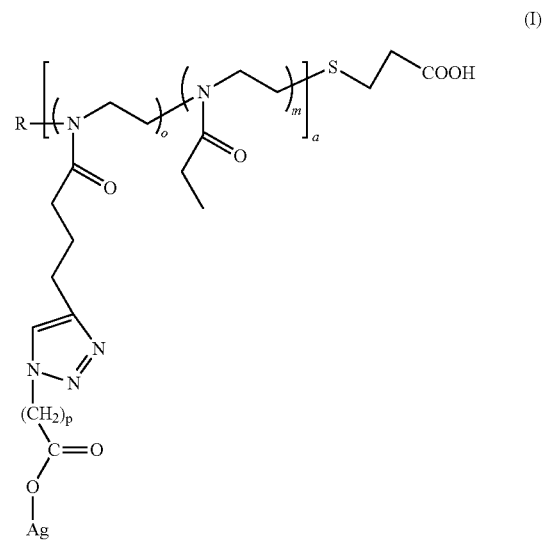

wherein,
a is ran which indicates a random copolymer or block which indicates a block copolymer
o is an integer from 1 to 50;
m is an integer from 190 to 950;
p is 1-18;
R is hydrogen, alkyl or substituted alkyl; and
Ag is a dopamine agonist selected from the group consisting of: rotigotine, pramipexole, quinagolide, fenoldopam, apomorphine, 5-OH-DPAT, ropinirole, pergolide, cabergoline, and bromocriptine.

2. The polymer conjugate of claim 1, wherein the dopamine agonist is rotigotine or (−)rotigotine.

3. The polymer conjugate of claim 1, wherein the poly(oxazoline) polymer has a molecular weight range of 300 Da to 200,000 Da.

4. The polymer conjugate of claim 1, wherein R is hydrogen.

5. The polymer conjugate of claim 1, wherein R is alkyl.

6. The polymer conjugate of claim 1 wherein the polymer conjugate has structure:

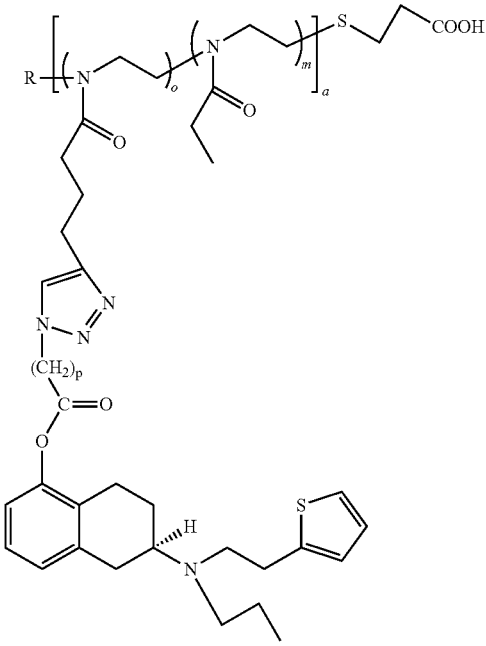

7. The polymer conjugate of claim 1, wherein the dopamine agonist is ropinirole.

8. The polymer conjugate of claim 1, wherein the polymer conjugate has structure:

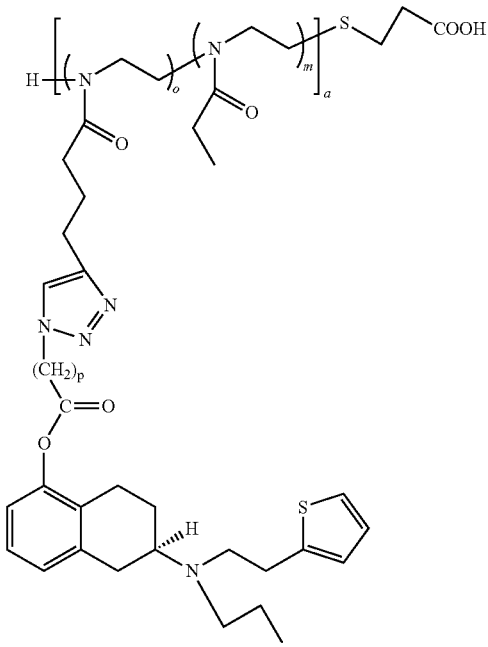

9. A method for treating a disease or condition related to dopamine insufficiency in the peripheral or central nervous system, the method comprising the step of administering to the subject an amount of a polymer conjugate, the polymer conjugate comprising a poly(oxazoline) polymer and an dopamine agonist, the dopamine agonist linked to the polymer by a releasable linker, the releasable linker cleavable in a subject and providing a sustained, controllable delivery of the dopamine agonist over a period of days to weeks.

10. The method of claim 9, wherein the dopamine agonist is rotigotine or (−)rotigotine.

11. The method of claim 9, wherein the dopamine agonist is ropinirole.

12. The method of claim 9, wherein the polymer conjugate is administered alone or as a part of a pharmaceutical composition.

13. The method of claim 9, wherein the polymer conjugate is administered in a therapeutically effective amount.

14. The method of claim 9, wherein the polymer conjugate is administered by subcutaneous administration.

15. The method of claim 9, wherein release of the dopamine agonist is controlled by the nature of the releasable linker, the size of the polymer, the method of delivery or a combination of the foregoing.

16. The method of claim 9, wherein the polymer conjugate has the structure

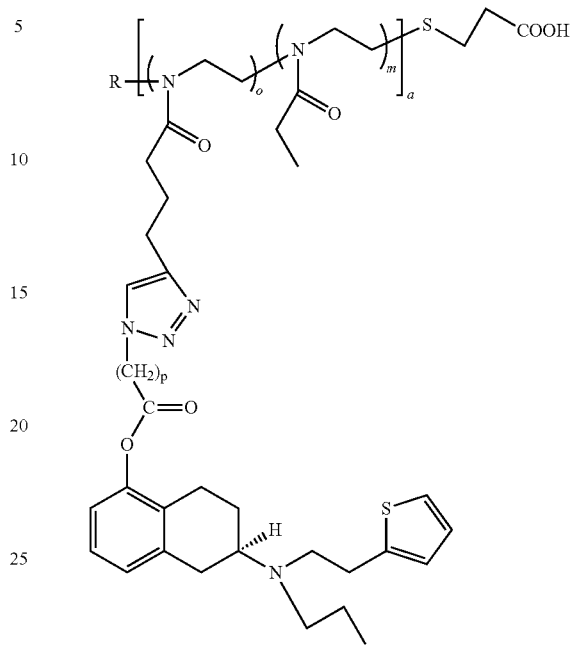

wherein
R is hydrogen, alkyl or substituted alkyl;
p is 1 to 18;
a is ran which indicates a random copolymer or block which indicates a block copolymer;
o is an integer from 1 to 50; and
m is an integer from 190 to 950.

17. A method for treating Parkinson's disease, the method comprising the step of administering to the subject an amount of a polymer conjugate, wherein the polymer conjugate has the structure

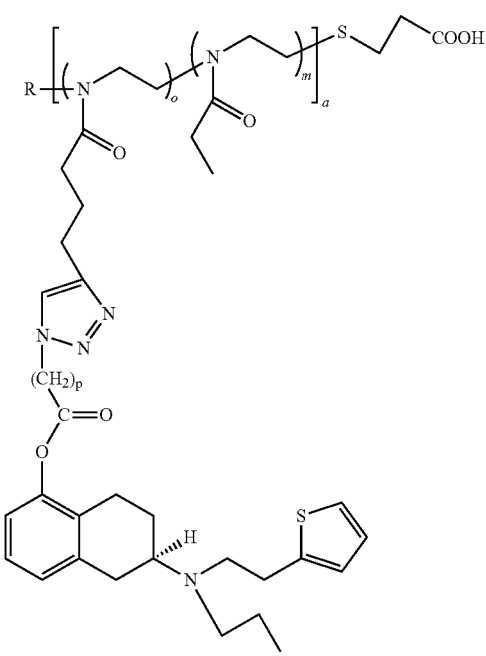

wherein
R is hydrogen, alkyl or substituted alkyl;
p is 1 to 18;
a is ran which indicates a random copolymer or block which indicates a block copolymer;
o is an integer from 1 to 50; and
m is an integer from 190 to 950.

* * * * *